(12) United States Patent
Esumi et al.

(10) Patent No.: US 9,907,852 B2
(45) Date of Patent: Mar. 6, 2018

(54) ANTICANCER AGENT AND SIDE-EFFECT-ALLEVIATING AGENT

(71) Applicants: National University Corporation University of Toyama, Toyama (JP); Kracie Pharma, Ltd., Tokyo (JP); National Cancer Center, Tokyo (JP); Tokyo University of Science Foundation, Tokyo (JP)

(72) Inventors: Hiroyasu Esumi, Tokyo (JP); Masafumi Ikeda, Chiba (JP); Katsuya Tsuchihara, Chiba (JP); Shigeki Chiba, Toyama (JP); Satoshi Yomoda, Toyama (JP); Takanori Kawashima, Toyama (JP); Toshiki Okubo, Toyama (JP); Yasuhiro Tezuka, Toyama (JP); Kenta Murata, Toyama (JP)

(73) Assignees: National University Corporation University of Toyama, Toyama (JP); Kracie Pharma, Ltd., Tokyo (JP); National Cancer Center, Tokyo (JP); Tokyo University of Science Foundation, Tokyo (JP)

( * ) Notice: Subject to any disclaimer, the term of this patent is extended or adjusted under 35 U.S.C. 154(b) by 0 days.

(21) Appl. No.: 15/302,863

(22) PCT Filed: Apr. 10, 2015

(86) PCT No.: PCT/JP2015/061296
§ 371 (c)(1),
(2) Date: Oct. 7, 2016

(87) PCT Pub. No.: WO2015/156409
PCT Pub. Date: Oct. 15, 2015

(65) Prior Publication Data
US 2017/0028065 A1 Feb. 2, 2017

(30) Foreign Application Priority Data
Apr. 10, 2014 (JP) ................. 2014-080895

(51) Int. Cl.
| A61K 31/34 | (2006.01) |
| A61K 36/00 | (2006.01) |
| A61K 47/22 | (2006.01) |
| A61K 36/28 | (2006.01) |
| A61K 31/7068 | (2006.01) |
| A61K 45/06 | (2006.01) |
| A61K 47/46 | (2006.01) |
| A61K 39/395 | (2006.01) |
| C07K 16/22 | (2006.01) |
| A61K 39/00 | (2006.01) |

(52) U.S. Cl.
CPC .......... *A61K 47/22* (2013.01); *A61K 31/7068* (2013.01); *A61K 36/28* (2013.01); *A61K 39/3955* (2013.01); *A61K 45/06* (2013.01); *A61K 47/46* (2013.01); *C07K 16/22* (2013.01); *A61K 2039/505* (2013.01); *C07K 2317/24* (2013.01); *C07K 2317/76* (2013.01)

(58) Field of Classification Search
CPC ........................... A61K 31/365; A61K 36/185
USPC .......................................... 514/473; 424/777
See application file for complete search history.

(56) References Cited

U.S. PATENT DOCUMENTS

2013/0190394 A1    7/2013  Zhao ................... A61K 31/365

FOREIGN PATENT DOCUMENTS

| CN | 102335429 A | 2/2012 | .......... A61K 31/198 |
| CN | 102370983 A | 3/2012 | .......... A61K 31/365 |
| CN | 102397547 A | 4/2012 | .......... A61K 31/365 |
| CN | 102397548   | 4/2012 | .......... A61K 31/365 |
| CN | 102805743   | 12/2012 | .......... A61K 31/365 |
| CN | 103417554   | 12/2013 | .......... A61K 31/365 |
| JP | 2013-542205 A | 11/2013 | .......... A61K 31/365 |
| JP | 2014-500095 A | 1/2014 | ............... A44C 5/00 |

OTHER PUBLICATIONS

Miyoshi, et al.(English translation within), "Arctigenin inhibits pancreatic tumor growth in combination with common chemotherapeutics," Proceedings of the Japanese Cancer Association, vol. 67, p. 347, 2008.

Japanese Patent Office, International Search Report pertaining to Application No. PCT/JP2015/061296, 2 pages, dated Jun. 9, 2015.

*Primary Examiner* — Raymond J Henley, III
(74) *Attorney, Agent, or Firm* — Sunstein Kann Murphy & Timbers LLP

(57) ABSTRACT

The purpose of the present invention is to provide an anticancer agent for potentiating an antitumor effect, alleviating side effects, and further extending the survival rate by concomitant use with a component having an anticancer effect. An anticancer agent combining arctigenin and a component other than arctigenin that has an anticancer effect, in which the anticancer agent may be a combination drug or may be a kit configured from a formulation containing arctigenin and a formulation containing a component that has an anticancer effect, and the concomitant use of arctigenin and the component having an anticancer effect more strongly inhibits tumor growth and reduces the proportion of cancer stem cells in the tumor, making it possible to extend the total survival time and to alleviate side effects caused by the component having an anticancer effect.

6 Claims, 9 Drawing Sheets

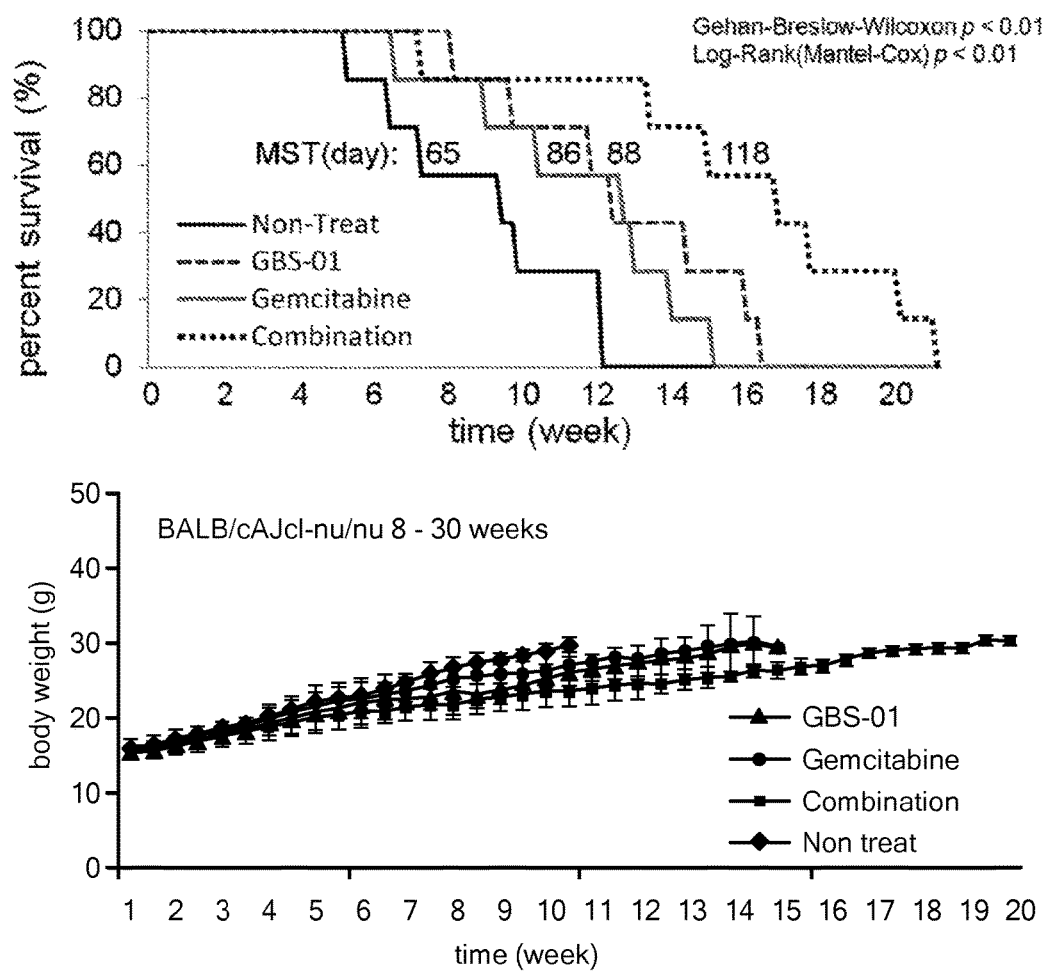
[Fig. 5]

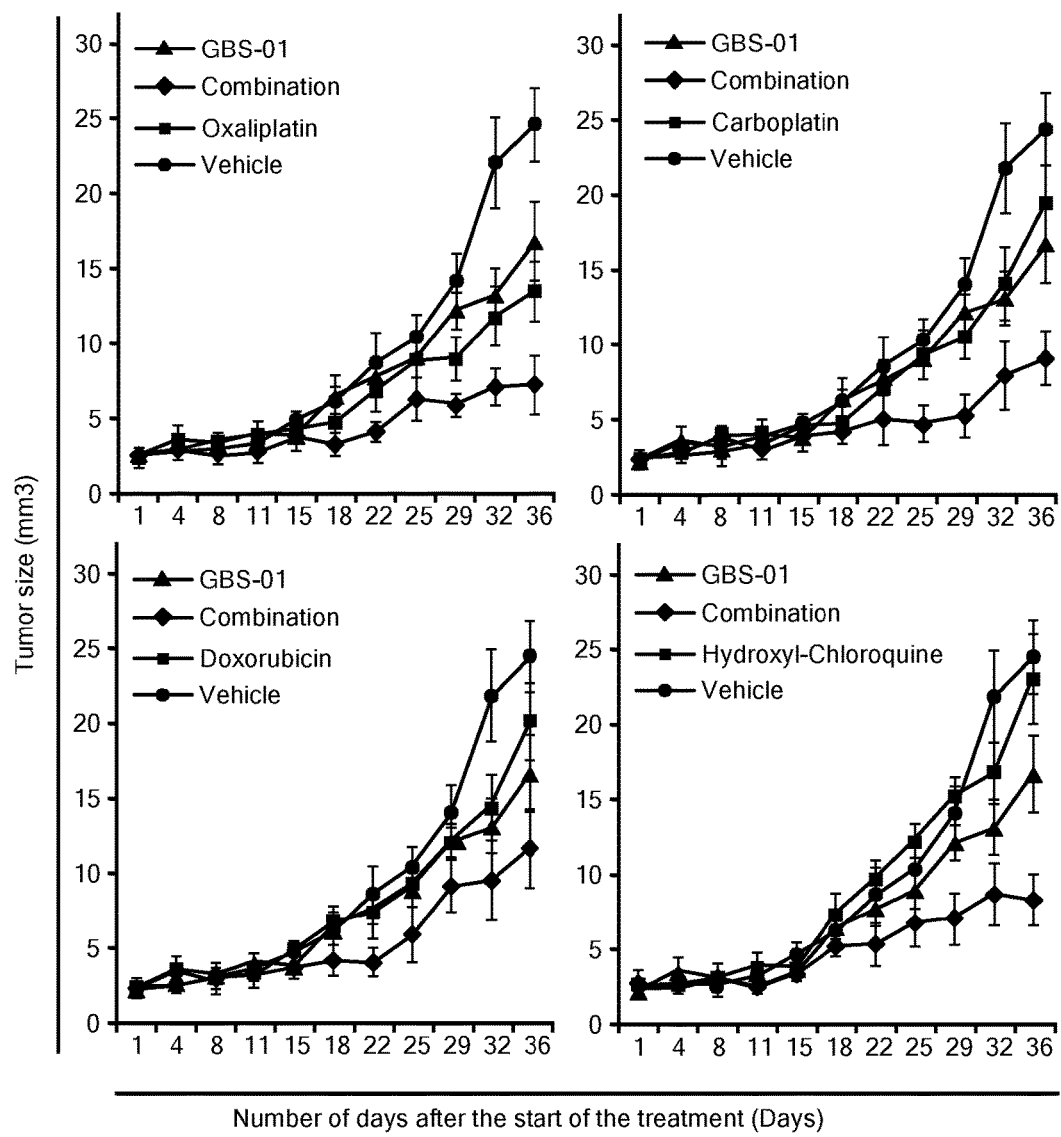
[Fig. 6-1]

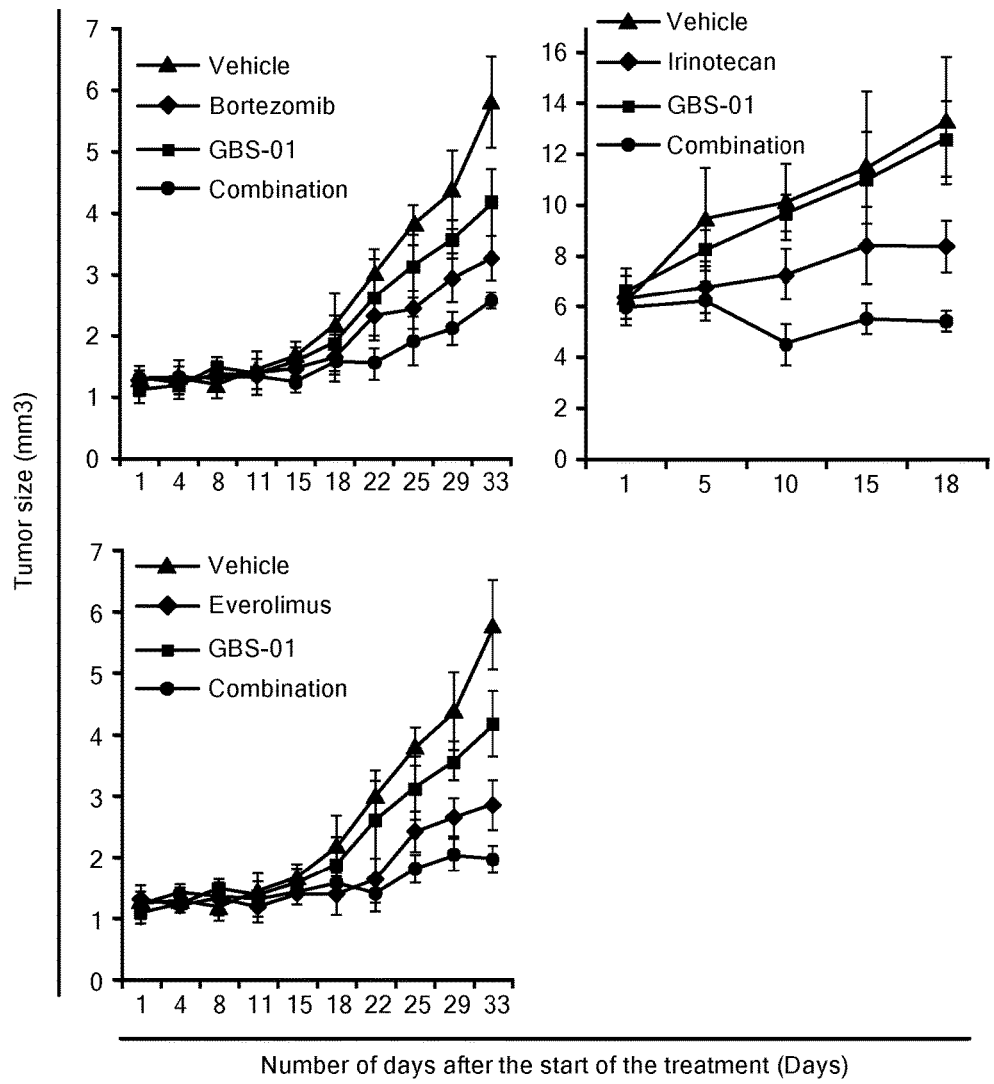
[Fig. 6-2]

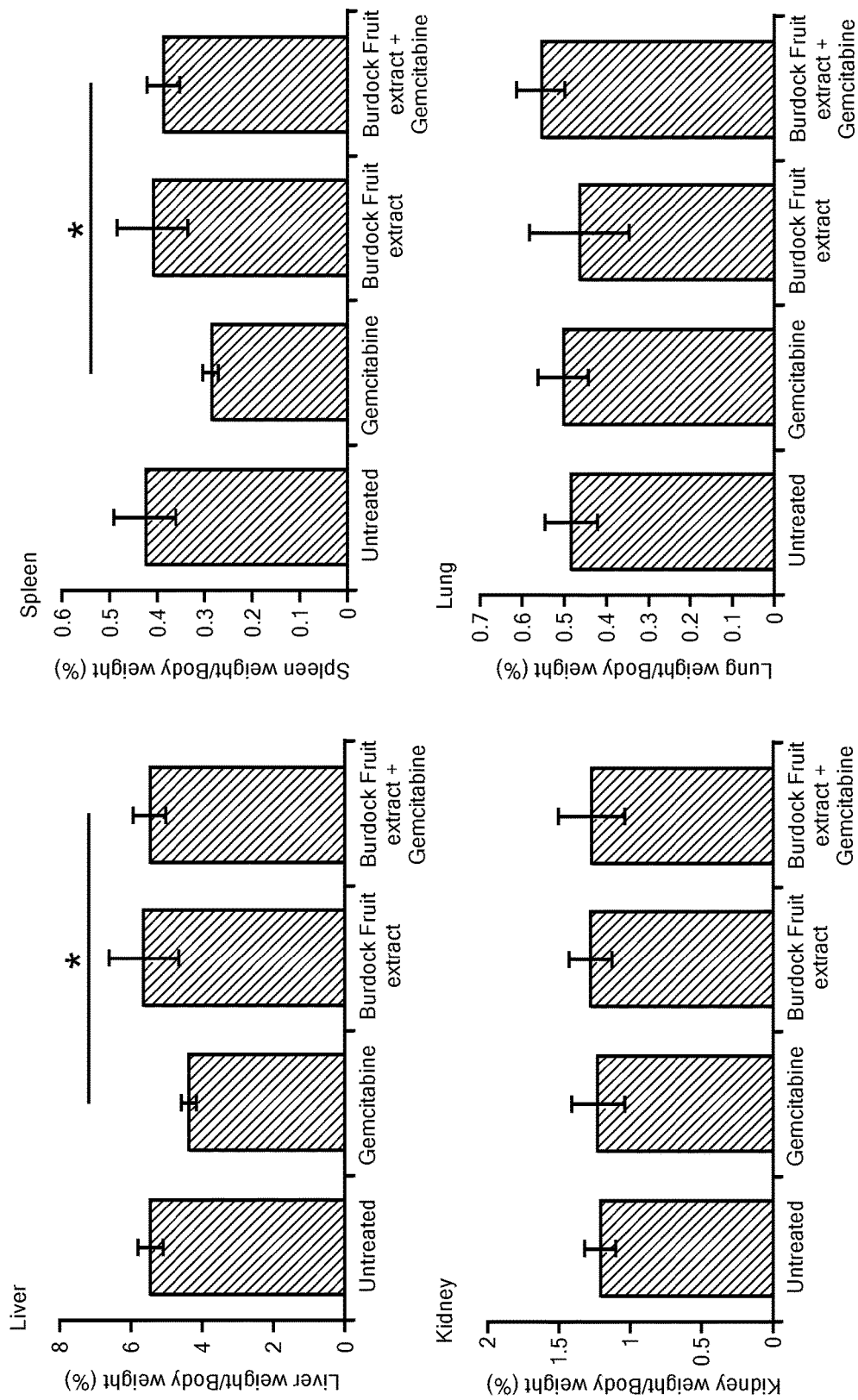
[Fig. 7A]

| Organ weight(g) | Liver weight(g) | Lung weight(g) | Kidney weight(g) | Spleen weight(g) |
|---|---|---|---|---|
| Untreated | 2.301 | 0.199 | 0.535 | 0.225 |
|  | 2.630 | 0.195 | 0.566 | 0.147 |
|  | 2.321 | 0.221 | 0.468 | 0.185 |
|  | 2.196 | 0.263 | 0.562 | 0.203 |
|  | 2.396 | 0.199 | 0.466 | 0.162 |
|  | 2.463 | 0.187 | 0.537 | 0.180 |
| Gemcitabine | 1.466 | 0.189 | 0.456 | 0.106 |
|  | 1.518 | 0.201 | 0.403 | 0.104 |
|  | 1.541 | 0.167 | 0.421 | 0.101 |
|  | 1.610 | 0.203 | 0.376 | 0.092 |
|  | 1.617 | 0.147 | 0.425 | 0.103 |
|  | 1.694 | 0.180 | 0.567 | 0.105 |
| Burdock Fruit extract | 2.270 | 0.188 | 0.552 | 0.201 |
|  | 1.907 | 0.198 | 0.601 | 0.144 |
|  | 2.064 | 0.107 | 0.469 | 0.138 |
|  | 1.902 | 0.235 | 0.523 | 0.129 |
|  | 2.732 | 0.231 | 0.432 | 0.172 |
|  | 2.797 | 0.162 | 0.484 | 0.194 |
| Burdock Fruit extract Gemcitabine | 1.801 | 0.221 | 0.378 | 0.153 |
|  | 2.184 | 0.215 | 0.393 | 0.129 |
|  | 2.208 | 0.239 | 0.430 | 0.154 |
|  | 1.960 | 0.190 | 0.601 | 0.154 |
|  | 1.927 | 0.184 | 0.517 | 0.136 |
|  | 2.145 | 0.194 | 0.512 | 0.131 |

Test data of the respective treatments

| Leukocyte | Erythrocyte | Hemoglobin | Hematocrit | Platelet | Protein | Albumin | AST | ALT | Urea nitrogen | Blood sugar | Total cholesterol | Total bilirubin |
|---|---|---|---|---|---|---|---|---|---|---|---|---|
| 3300±14300 /mm³ | 926±44.3 X10⁴/mm³ | 15±0.84 g/dl | 47±3.01% | 118±22.18 X10⁴/mm³ | 4.8±0.11 g/dl | 3.6±1.4 g/dl | 78±13.4 IU/L *CLEA | 46±24.9 IU/L *CLEA | 21.5±3.9 mg/d | 89±20.6 mg/dl *CLEA | 92±9.1 mg/dl | 0.26±0.14 mg/dl *CLEA + SLC |
| 2100 | 860 | 13.6 | 42.1 | 67.3 | 4.7 | 4.7 | 81 | 36 | 18 | 62 | 64 | 0.1 |
| 2200 | 805 | 13.2 | 41 | 113 | 3.5 | 3.5 | 67 | 29 | 21 | 72 | 93 | 0.1 |
| 3000 | 865 | 15.4 | 38.8 | 122.2 | 4 | 3.3 | 87 | 33 | 24 | 85 | 82 | 0.1 |
| 1900 | 767 | 12.1 | 40.5 | 63.7 | 4.5 | 4 | 74 | 26 | 23 | 68 | 64 | 0.3 |
| 5500 | 754 | 12.4 | 37.5 | 72.2 | 3.8 | 3.8 | 91 | 44 | 18 | 77 | 98 | 0.1 |
| 2200 | 798 | 13.2 | 43 | 86.1 | 4.7 | 4 | 83 | 32 | 25 | 82 | 114 | 0.1 |
| 2816.67 | 808.17 | 13.32 | 40.48 | 87.42 | 4.20 | 3.87 | 80.50 | 33.33 | 21.50 | 71.00 | 85.83 | 0.13 |
| 1367.36 | 46.17 | 1.16 | 2.05 | 24.76 | 0.51 | 0.50 | 8.76 | 6.25 | 3.02 | 8.99 | 19.80 | 0.08 |
| 3000 | 803 | 13.5 | 35.5 | 119.4 | 3.8 | 3.4 | 88 | 46 | 25 | 112 | 83 | 0.1 |
| 3100 | 729 | 11.9 | 36.1 | 90.5 | 4.3 | 4.3 | 72 | 28 | 25 | 68 | 91 | 0.1 |
| 2900 | 893 | 14.3 | 43.7 | 74.6 | 4.5 | 4.3 | 92 | 26 | 28 | 72 | 84 | 0.1 |
| 2800 | 835 | 13.7 | 40.4 | 94.8 | 4.3 | 3.5 | 59 | 31 | 21 | 69 | 73 | 0.1 |
| 2600 | 844 | 13.3 | 42.5 | | 4.7 | 3.8 | 74 | 27 | 30 | 104 | 84 | 0.1 |
| 3700 | 879 | 14.1 | 46.6 | 101 | 4.8 | 3.9 | 76 | 29 | 30 | 75 | 103 | 0.1 |
| 3050.00 | 830.50 | 13.47 | 40.80 | 96.06 | 4.40 | 3.87 | 76.83 | 31.17 | 26.50 | 83.33 | 86.33 | 0.10 |
| 339.12 | 59.19 | 0.85 | 4.37 | 16.30 | 0.36 | 0.36 | 11.87 | 7.47 | 3.51 | 19.43 | 9.99 | 0.00 |
| 1200 | 640 | 10.6 | 33.2 | 54.4 | 4.1 | 3.2 | 137 | 94 | 16 | 73 | 85 | 0.5 |
| 1000 | 712 | 11.1 | 33.2 | | 4.2 | 3.1 | 93 | 26 | 17 | 85 | 72 | 0.2 |
| 1500 | 567 | 13.8 | 37.2 | 59.7 | 2.6 | 3.6 | 96 | 48 | 14 | 81 | 70 | 0.3 |
| 1200 | 775 | 11.6 | 33.5 | 64 | 4.7 | 3.1 | 82 | 59 | 18 | 54 | 54 | 0.2 |
| 1200 | 752 | 11.9 | 38.6 | 55.8 | 4.8 | 3.9 | 164 | 86 | 15 | 104 | 81 | 0.4 |
| 2500 | 763 | 9.4 | 31.2 | 74.2 | 2.8 | 3.1 | 134 | 82 | 12 | 88 | 116 | 0.2 |
| 1433.33 | 701.50 | 11.40 | 34.48 | 61.58 | 3.90 | 3.33 | 117.67 | 67.50 | 15.33 | 82.50 | 79.67 | 0.30 |
| 546.50 | 82.12 | 1.47 | 2.81 | 8.00 | 0.94 | 0.34 | 32.05 | 27.93 | 2.16 | 17.63 | 20.79 | 0.13 |
| 2200 | 797 | 12.9 | 38.6 | 111.4 | 4.1 | 3.2 | 112 | 68 | 20 | 76 | 66 | 0.3 |
| 2100 | 892 | 11.7 | 39.1 | 63.5 | 3.9 | 3.2 | 88 | 31 | 16 | 81 | 68 | 0.3 |
| 1700 | 801 | 12.7 | 39.2 | 76.7 | 4.5 | 3.3 | 85 | 35 | 23 | 75 | 107 | 0.5 |
| 2600 | 802 | 12.7 | 36.3 | 55.2 | 2.9 | 2.5 | 74 | 24 | 20 | 80 | 71 | 0.2 |
| 2300 | 774 | 12.9 | 39 | 83.3 | 4.2 | 3.2 | 84 | 38 | 21 | 92 | 77 | 0.2 |
| 2000 | 821 | 12.5 | 38.2 | 113.2 | 4.2 | 3.4 | 117 | 81 | 19 | 75 | 108 | 0.1 |
| 2150.00 | 814.50 | 12.57 | 38.40 | 80.55 | 3.97 | 3.13 | 95.00 | 46.17 | 19.83 | 79.83 | 82.83 | 0.27 |
| 301.66 | 40.83 | 0.45 | 1.09 | 25.55 | 0.56 | 0.32 | 16.52 | 22.82 | 2.32 | 6.49 | 19.47 | 0.14 |

ANTICANCER AGENT AND SIDE-EFFECT-ALLEVIATING AGENT

CROSS REFERENCE

This application is a national phase entry of the international application PCT/JP2015/061296 filed on Apr. 10, 2015, which derives priority from Japanese patent application No: 2014-080895 filed on Apr. 10, 2014, the contents of each of which are herein incorporated by reference in their entirety.

TECHNICAL FIELD

The present invention relates to a new anticancer agent and a side effect-alleviating agent for reducing the side effects caused by a component having an anticancer activity.

BACKGROUND ART

Cancers (malignant tumors) now occupy approximately 30 percent of the cause of death in Japan. In particular, pancreas cancer is one of intractable cancers, the 5 year-survival rate of the all patients is estimated to be 2 to 3%. The number of patients died of pancreas cancer has rapidly been increased approximately 2.5 times during a period of the last 20 years, and according to the statics in 2009, 26,791 patients died of pancreas cancer. The number of onset is approximately the same as the number of death, which occupies 6% of the cause of death due to cancers in Japan, and the number of death in pancreas cancer is ranked in fifth position following the cancers in other regions, lung, stomach, large intestine, and liver.

Therapy by which a radical cure is expected depends only on surgical excision, but as the pancreas cancer is found in a state of progressive cancer (stage III+IV) in most of the patients, it is practically said that the cases in which radical excision can be applied are at most 10-20% of the total patients of pancreas cancer. For every stages, the median of the survival period is about 12-30 months in the stages I and II, 9-11 months in the stage III, and 5-6 months in the stage IV, indicating that the prognosis is extremely poor and it is considered that there is almost no possibility to cure particularly inpatients with the pancreas cancer which cannot be excised.

The standard therapy for a progressive pancreas cancer is based on gemcitabine, and when gemcitabine results in a refractory state, there is no standardized therapy established. In some progressive pancreas cancer patients, a general condition seems well even after they become refractory to gemcitabine. It has been considered accordingly that development of an effective therapeutic method in such a group of patients (pancreas cancer refractory to gemcitabine) is an important problem all over the development of a therapeutic method for pancreas cancer.

In recent years, it has been reported that the cells derived from pancreas cancer such as PANC-1, AsPC-1, BxPC-1 and KP-3 show a strong resistance even in an extreme nutritional deficiency state, and the removal of this resistance would possibly lead to a new biochemical approach in the cancer therapy (Patent Document 1: which is hereby incorporated by reference in its entirety).

It has been reported that arctigenin is effective in a screening of substances which can remove the viability of tumor cells in a low nutritional state using a pancreas cancer cell strain PANC-1 (Non-Patent Document 1: which is hereby incorporated by reference in its entirety).

In addition, the cancer stem cells have self-replication competence and pluripotency, and thus exhibit a strong tumor-producing ability to form cancers from a small number of cells at a high rate.

It has been pointed out that in tumor tissues a large number of immature blood vessels are formed with sudden increase of the tissues, resulting in circulatory failure in the tissues to cause not only hypoxia and undernutrition but also the influence on the delivery of anticancer agents. On the other hand, the cancer stem cells show resistance to a number of anticancer agents and radiation and cause metastasis, which greatly disturb the cancer therapy. It is known that the stem cells are highly induced in such a specific micro-environment as especially hypoxia and undernutrition among the cancer tissue.

Accordingly, it is considered that the development of a therapeutic method for targeting the cancer stem cells or a method for normalizing the blood vessel by inhibition of angiogenesis might greatly contribute to the anticancer therapy.

CITATION LIST

Patent Literature

PTL 1: JP-A-2002-065298

Non-Patent Literature

NPL 1: S. AwaLe, J. Lu, S. K. KaLauni, Y. Kurashima, Y. Tezuka, S. Kadota, H. Esumi, Cancer Res., 2006, 66(3), 1751-1757)

SUMMARY OF INVENTION

Technical Problem

In general, anticancer agents are accompanied by many side effects such as decrease of body weight, decrease of organ weight, inflammation of skin and mucous membrane, hair loss, diarrhea, and cytopenia. It is known that gemcitabine which is, an anticancer agent for pancreas cancer, also causes such side effects as myelosuppression and liver damage. Accordingly, it has been desired to develop an anticancer agent having not only a much more active anticancer activity but also low side effect.

The purpose of the present invention is to provide an anticancer agent having a higher anticancer activity and capable of reducing its side effect and to provide an agent for alleviating the side effect.

Solution to Problems

The present inventors have found that when a combined preparation of a Burdock Fruit (arctii fructus) extract containing arctigenin and gemcitabine is administered to mice transplanted human pancreas cancer cells, increase of the tumor weight is suppressed and still more the intra-tumor proportion of $CD44^+$, $CD24^+$ and $CD326^+$ cells (triple positive) as well as $CD133^+$ and $CD44^+$ cells (double positive) is significantly decreased compared to those of untreated group and a single administration group witch have been reported as cancer stem cell fractions in pancreas cancer. In addition, it has been found that in the combined administration the side effect is improved which is seen in a single administration of gemcitabine. In addition, it has been also found that the total survival period is markedly prolonged by the administration of a combination of a Burdock Fruit extract and gemcitabine.

In addition, it has been found that the administration of arctigenin suppress angiogenesis in immature vessels, while it leads to necrosis of a hypoxic and undernutritional intra-tumor region formed by immature vessels, resulting in normalization of the blood stream in the tumor tissue; thus, it is considered that the drug delivery of a component having an anticancer effect into the tumor tissues is improved. The angiogenesis in tumor tissues is induced by release of an angiogenesis factor from cancer cells or tumor interstitial cells by stimulation with hypoxia or hypoglycemia or growth factor. In the micro-environment of cancer, there are abundant angiogenesis factors such as VEGF (vascular endothelial growth factor) which induce such angiogenesis. Bevacizumab (Avastin etc.), an antibody inhibiting VEGF, inhibits the angiogenesis in tumors. Bevacizumab, however, gives an influence not only to tumor vessels but also to normal blood vessels, having some problems of side effect such as hemorrhage and thrombus. Further, it has been pointed out that the effect of normalization of the tumor vessels and improvement of the blood stream is transient, and a hypoxic state caused by retraction of blood vessels thereafter makes the cancer cells malignant again.

On the other hand, it is considered that arctigenin reduces the tissues containing cancer cells and cancer stem cells which survive under hypoxia/undernutrition environment in tumor tissues, while the release of angiogenesis factors which is induced under hypoxia/undernutrition is suppressed as a result. Therefore, it is considered that arctigenin leads the improvement of the delivery of an anticancer component into tumors because it can selectively normalize the blood vessels in tumors. This effect is considered to be caused by that arctigenin moves to a hypoxia/undernutritional region of tumor tissues through interstitial fluid or lymph which has leaked from capillary to kill and damage malignant cancer cells or cancer stem cells.

It became clear that arctigenin also enhances the effect of bevacizumab when used in combination with a VEGF inhibitor, bevacizumab. Namely, it was found that when a Burdock Fruit extract containing arctigenin was administered to mice transplanted a human colorectal cancer cell, in combination with an existing anticancer agent, bevacizumab, for colorectal cancer, an increase of tumor weight was much more strongly suppressed compared with that of an untreated group and that of a single administration group. In addition, the combination of arctigenin led highly malignant tumor tissues to necrosis in a hypoxia and undernutritional environment and was suppressed the formation of ulcers in the tissues by the suppression of the angiogenesis in immature tumors (see: FIG. 2). This indicates that the blood stream has been improved in the tumors and that the delivery of anticancer agents administrated in combination has also been improved. Thus, the present inventors found that arctigenin could enhance the effect of a component having an anticancer effect by these effects.

In addition, it was found that a Burdock Fruit extract containing arctigenin, when administered in combination with a variety of anticancer components to mice transplanted to which human pancreas cancer, much more strongly inhibited an increase of the tumor volume compared with that of an untreated group and that of a single administration group. The present invention was completed by the present inventors on the basis of these findings.

Namely, the present invention provides an anticancer agent which includes arctigenin in combination with a component having an anticancer activity other than arctigenin.

In addition, the present invention provides the anticancer agent as described above which is a combination drug.

In addition, the present invention provides an anticancer agent which is a kit including a pharmaceutical preparation containing arctigenin and a pharmaceutical preparation containing a component having an anticancer effect in the above described anticancer agent.

In addition, the present invention provides an anticancer agent as described in the above anticancer agent wherein the arctigenin is a Burdock Fruit extract.

In addition, the present invention provides a pharmaceutical preparation which contains arctigenin as an active component and is administered in combination with a component having an anticancer effect other than arctigenin.

In addition, the present invention provides an agent for alleviating a side effect which contains arctigenin as an active component to alleviate the side effect caused by a component having anticancer effect other than arctigenin.

In addition, the present invention provides an agent for normalizing the intra-tumor blood vessels which contains arctigenin as an active component.

In addition, the present invention provides an agent for enhancing the drug delivery of an active component having an anticancer effect to tumor tissues which contains arctigenin as an active component.

Advantageous Effects of Present Invention

In the present invention, arctigenin is administered in combination with a component having an anticancer effect other than arctigenin and thereby inhibit the increase of tumors and reduce the proportion of the cancer stem cells in tumors, exhibiting a higher anticancer activity.

In addition, according to the present invention, it is possible to alleviate the side effect resulting from conventional anticancer agents. In addition, according to the present invention, it is possible to prolong the total survival period compared with a single administration of conventional anticancer agents.

BRIEF DESCRIPTION OF DRAWINGS

FIG. 5 shows the survival rate after administration of the concomitant preparation according to the embodiment of the present invention to mice orthotopically transplanted pancreas cancer.

FIG. 6-1 shows the variation of the tumor size caused by administration of the existing chemotherapeutic agents, a Burdock Fruit extract rich in arctigenin and a concomitant preparation of them, to a model of pancreas cancer.

FIG. 6-2 shows the variation of the tumor size caused by administration of the existing chemotherapeutic agents, a Burdock Fruit extract rich in arctigenin and a concomitant preparation of them, to a model of pancreas cancer.

FIGS. 7A-7B shows the result of weight measurement of kidney, liver, spleen and lung and the rate (%) of their weight/body weight after administration of the concomitant preparation according to the embodiment of the present invention.

FIG. 8 shows the results of the tests conducted on hemocytes and the biochemical tests after administration of the concomitant preparation according to the embodiment of the present invention.

DESCRIPTION OF EMBODIMENTS

[Anticancer Agents]

Figure 1:
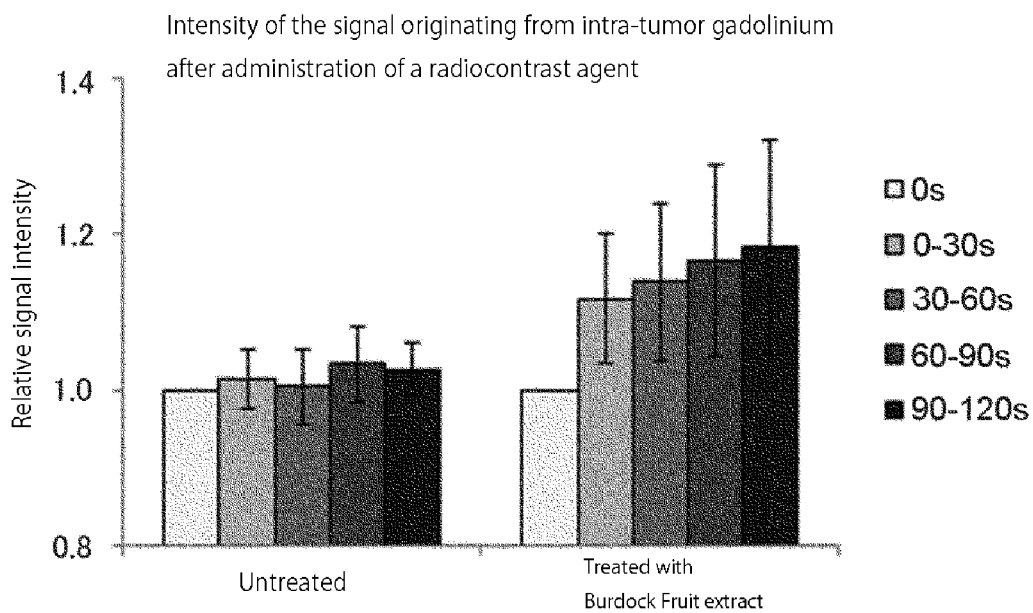
FIG. 1 shows a state of an intra-tumor blood stream after administration of a Burdock Fruit extract rich in arctigenin.

The anticancer agent of the present invention is a preparation of arctigenin as an active component combined with other component(s) having an anticancer activity other than arctigenin. In other words, the anticancer agent of the present invention is a preparation containing a component with an anticancer activity other than arctigenin combined with arctigenin as an enhancer for drug delivery of said component to tumor tissues. That is, the anticancer agent of the present invention is a concomitant preparation administered in combination of arctigenin and a component having an anticancer activity.

The anticancer agent of the present invention is a pharmaceutical preparation having an anticancer activity, which contains arctigenin as an active component. The anticancer activity possessed by the anticancer agent of the present invention not only suppressing the growth of cancer cells or reducing the number of them but also reducing of the number of cancer stem cells.

The cancer stem cells include cancerous cells having a stem-cell property among cancer cells, which provide with an autonomous replicating ability and an ability supplying precursor cells. The cancer stem cells have an ability which supplies cancer cells to reconstruct the tumor tissues. The anticancer agent of the present invention not only suppresses the growth of cancer cells but also reduces the number of cancer stem cells, and thus they can contribute to prevention of the onset, metastasis and recurrence of cancers.

A variety of markers are known as to the cancer stem cells. Among the cancer stem cells in pancreatic tumors, the $CD44^+$, $CD24^+$ and $CD326^+$ cells (triple positive) are excellent in making tumors. In addition, among the intra-tumor cancer stem cells, the $CD133^+$ and $CD44^+$ cells (double positive) have a very high metastatic property.

In addition, the cancer stem cell is considered to exist abundantly in a peculiar micro-environment such as hypoxia and undernutrition. In such an environment, it is considered that as a large number of immature tumor blood vessels are formed by induction with hypoxia and hypoglycemic signal, circulatory failure occurs readily to make delivery of the anticancer agent worse and decrease its anticancer activity. Therefore, it is considered that removal of the cancer cells around the deficient region including immature blood vessels could suppress angiogenesis to normalize the blood stream, making the anticancer agent effective.

In this specification, the "combination" of arctigenin and a component having an anticancer activity other than arctigenin includes providing them as combination drugs, providing pharmaceutical preparations as kits containing respective components, and combined use of these components. In this specification, the term "combine" with a component having an anticancer activity other than arctigenin means the administration of arctigenin before or concurrent with or after the administration of the component having an anticancer activity. As far as both of arctigenin and a component having an anticancer activity other than arctigenin are used, there is no limitation in the order or the dosage form.

Such dosage form includes administration of a single preparation obtained by concurrent formulation of arctigenin and a component having an anticancer activity, concurrent administration in the same route of administration of two kinds of preparations obtained by separate formulation of arctigenin and of a component having an anticancer activity, administration at intervals over time in the same route of administration of two kinds of preparations obtained by separate formulation of arctigenin and of a component having an anticancer activity, concurrent administration through a different route of administration of two kinds of preparations obtained by separate formulation of arctigenin and of a component having an anticancer activity, and administration at intervals over time through a different route of administration of two kinds of preparations obtained by separate formulation of arctigenin and of a component having an anticancer activity.

The component having an anticancer activity other than arctigenin may be any pharmaceutical preparations having an anticancer activity, for example, existing anticancer agents may be used. The components having an anticancer activity used in the present invention have an anticancer activity against the following cancers: breast cancer, prostatic cancer, pancreas cancer, gastric cancer, lung cancer, colon cancer, rectal cancer, colorectal cancer, cancer of small intestine, esophageal cancer, duodenal cancer, lingual cancer, pharyngeal cancer, cancer of salivary gland, brain tumor, neurilemmoma, liver cancer, renal cancer, gallbladder carcinoma, carcinoma of bile duct, carcinoma of pancreas, hepatic cancer, endometrial carcinoma, cancer of the uterine cervix, ovary cancer, cancer of bladder, cancer of urethra, skin cancer, angioma, malignant lymphoma, malignant melanoma, thyroid cancer, parathyroid cancer, nasal cavity cancer, nasal sinus cancer •, bone tumor, angiofibroma, retinal sarcoma, penile cancer, testicular tumor, infantile solid cancer, Kaposi sarcoma, maxillary sinus neoplasm, fibrous histiocytoma, leiomyosarcoma, rhabdomyosarcoma, and leukemia. The component having an anticancer preferably activity exhibits an anticancer activity against pancreas cancer and colon cancer.

As for the components having an anticancer activity, there is no particular limitation in the types of compounds as far as these contribute to suppression of the growth or metastasis of cancer cells as well as to the kill and wound of cancer cells or the suppression of the generation of cancer cells. The components having an anticancer activity may act on cancer cells in any way, directly or indirectly. The components having an anticancer activity used in the present invention can be, but not limited to cancerous antibiotics, platinum preparations, alkylating agents, antimetabolites, plant alkaloids, molecular target drug and hormone preparations. The components having an anticancer activity concomitantly used in the present invention can be, for example, 6-mercaptopurine, AC-T therapy, AC therapy, CAF therapy, CMF therapy, FOLFIRINOX therapy, FOLFIRI therapy, FOLFOX therapy, IRIS therapy, L-asparaginase, TS-1, UFT, XELOX therapy, actinomycin, aclarubicin, asparaginase, anastrozole, abiraterone, afatinib, affinitak, amrubicin, alectinib, idarubicin, ipilimumab, ifosfamide, ibritumomab, ibrutinib, ifosfamide, imatinib, immunobladder, irinotecan, interferon α, interferon β, interferon-γ, exemestane, ethinyl, etoposide, enocitabine, epirubicin, everolimus, eribulin, erlotinib, enzalutamide, oxaliplatin, cabazitaxel, capecitabine, carfilzomib, carboquone, carboplatin, carmofur, crizotinib, krestin, chlormadinone, gefitinib, gemcitabine, gemtuzumab ozogamicin, goserelin, thalidomide, cyclophosphamide, cisplatin, cytarabine, zinostatin stimalamer, sunitinib, cetuximab, ceritinib, sorafenib, daunorubicin, dacarbazine, tamoxifen, dasatinib, tamibarotene, tamoxifen, thiotepa, tegafur, degarelix, temsirolimus, temozolomide, doxifluridine, dexamethasone, doxorubicin, docetaxel, trastuzumab, trifluridine•tipiracil, tretinoin, toremifene, nivolumab, nimustine, nilotinib, neocarzinostatin, nedaplatin, nogitecan, paclitaxel, pazopanib, panitumumab, palbociclib, vandetanib, bicalutamide, picibanil, hydroxyurea, vinorelbine, pirarubicin, vincristine, vindesine, vinblastine, busulfan, fluorouracil, flutamide, fludarabine, fulvestrant, bleomycin, prednisone, prednisolone, procarbazine, bevacizumab, pepleomycin, pemetrexed, pertuzumab, bosutinib, bortezomdb, mitomycin, methotrexate, melphalan, ranimustine, lapatinib, rituximab, ribosomal doxorubicin, leuprolide, leuprorelin, ruxolitinib, regorafenib, letrozole, levofolinate, lenvatinib, and nab-paclitaxel. The anticancer agents of the present invention may contain only one member of components having an anticancer activity or a plurality of components having an anticancer activity.

The anticancer agents of the present invention can achieve much better anticancer effect by combining arctigenin with a component having an anticancer activity other than arctigenin and have an effect that the side effect caused by a component having an anticancer activity can be alleviated.

The side effect caused by a component having an anticancer activity is referred to an effect which does not meet the purpose of therapy or is inappropriate for living organisms, including the side effects generally recognized. For example, the side effect caused by a component having an anticancer activity includes a condition such as dermatitis, mucitis, depilation, diarrhea, anorexia, general malaise, pain, respiratory distress, retching, vomiting, fever, anosmia, organ damage, interstitial pneumonia, organ dysfunction and myelosuppression. In addition, mental anguish caused by these somatic damages such as anxiety, impatient, loss of interest, torpor of emotion, sleeplessness, sense of alienation, fear, maladjustment, depression and delirium, is included in the side effects of the component having an anticancer activity. In particular, the anticancer agent of the present invention can relieve organ damage such as myeloid suppression and hepatic damage can be relieved.

In this specification, the term "alleviating" of the side effect of a component having an anticancer activity refers to reducing and relieving the burden or pain caused by administration of the component having an anticancer activity in the organism. Namely, the term "alleviating" of the side effect refers to leads the adverse reaction to normalization. The "alleviating" of the side effect includes improving and curing the side effect once occurred, as well as preventing, suppressing and inhibiting the side effect before occurring.

The anticancer agent of the present invention may contain arctigenin so that arctigenin is administered at a dose of 10 to 2,000 mg a day for an adult.

In addition, the component having an anticancer activity may be contained in the anticancer agent at a dosage so that it can exhibit the anticancer activity. The dosage which can produce the anticancer activity depends on the component having an anticancer activity and can be established appropriately. For example, when the component having an anticancer activity is gemcitabine, it maybe contained in the anticancer agent so that the daily dosage becomes 500 to 2,000 mg/mm$^2$. Likewise, when the component having an anticancer activity is bevacizumab (Avastin), it may be contained in the anticancer agent so that the daily dosage becomes 5 to 30 mg/kg.

Arctigenin may be administered, but not limited to, for 1 to 7 days a week. For example, arctigenin may be administered every day or 5 to 6 times a week. The component having an anticancer activity may be also administered, but not limited to, for 0 to 7 days a week. For example, the component having an anticancer activity may be administered once a week.

For example, when arctigenin and the component having an anticancer activity are administered as combination of respectively different preparations, the preparation containing arctigenin and the preparation containing a component having an anticancer activity may be administered at the same time, or alternatively the preparation containing a component having an anticancer activity may first be administered and thereafter the preparation containing arctigenin may be administered, and the preparation containing arctigenin may first be administered and thereafter the preparation containing a component having an anticancer activity may be administered. When the administration is made at time intervals, the time interval depends on the dosage form, the way of administration and the variety of the component having an anticancer activity. Thus, the preparation containing arctigenin may be administered every day, while the preparation containing a component having an anticancer activity other than arctigenin maybe administered every 1 day to 28 days, every 1 day to 14 days, or every 1 day to 7 days. Conversely, the preparation containing a component having an anticancer activity other than arctigenin may first be administered.

In the anticancer agents of the present invention, when the component having an anticancer activity other than arctigenin is gemcitabine, for example, arctigenin may be administered at a dose of 10 to 2,000 mg a day for an adult for 5 to 6 days a week, while gemcitabine may be administered at a dose of 500 to 2,000 mg/mm$^2$ a day once a week. More preferably, arctigenin is administered at a dose of 100 to 500 mg a day for 5 to 6 days a week, while gemcitabine may be administered at a dose of 1,000 mg/mm$^2$ or more a day at least once a week.

In the anticancer agents of the present invention, when the component having an anticancer activity other than arctigenin is bevacizumab (Avastin), for example, arctigenin may be administered at a dose of 10 to 2,000 mg a day for an adult for 5 to 6 days a week, while bevacizumab may be administered at a dose of 5 to 30 mg/kg a day once a week. More preferably, arctigenin is administered at a dose of 100 to 500 mg a day for 5 to 6 days a week, while bevacizumab may be administered at a dose of 15 mg/kg or more a day at least once a week.

Arctigenin may be derived from a plant which contains arctigenin. The plant containing arctigenin includes, but not limited to, burdock (sprout, leaf, rhizome, fruit), safflower, cornflower, *Cirsium vulgare*, holy thistle (spotted thistle), cardoon, *Onopordum acanthium, Aniurokoazami, Forsythia×intermedia, Forsythia ovata,* forsythia, *Forsythia viridissima*, sesame, *Ipomoea cairica, Polygala polifolia, Trachelospermum asiatium, Trachelospermum asiaticum, MuninTeikakazura, Trachelospermum gracilipes, Trachelospermum jasminoides, Trachelospermum jasminoides* var. *Pubescens, Wikstroemda indica, Persicaria orientalis*, wild cherry blossoms, *Arabidopsis thaliana*, amaranthe, walnut, oats, spelt wheat, soft wheat, *Cupressus lusitanica* and Japanese torreya. In particular, burdock (particularly Burdock Fruit) and *forsythia* are preferred, since they are rich in arctigenin.

Burdock Fruit has been defined as the fruits of burdock (*Arctium lappa* Linne) in the Japanese Pharmacopoeia 16. In addition, Burdock Fruit is a crude drug which has been prescribed in Gingyosan, Kuhu-gedokuto (carminative antidotal Chinese drug), Syohusann, etc., and divided into an essential component which is used as pharmaceutical products exclusively. Burdock Fruit contains about 7% of arctiin (classified into lignin glycoside) and about 0.6% of arctigenin (an aglycon of arctiin).

In the present invention, when arctigenin is derived from Burdock Fruit, an extract of Burdock Fruit may be used, which extract can be obtained by employing a method for producing a Burdock Fruit extract as mentioned below. Therefore, it is possible to increase productivity during the production, and thus the anticancer agent can be produced conveniently at low cost. Further, when a plant other than Burdock Fruit is used, it is also possible to produce an extract containing arctigenin easily by utilizing a production method as mentioned below.

The powdered extract prepared according to a process for producing a Burdock Fruit extract as mentioned below contains arctigenin at a high level. Therefore, if the powdered extract prepared according to this process for producing a Burdock Fruit extract is used, it would be possible to obtain an anticancer agent having an excellent effect.

In addition, the anticancer agent of the present invention may further contain arctiin. Arctiin may be derived from a plant containing arctiin, for example, Burdock Fruit, burdock sprout, *forsythia* or *Forsythia viridissima*. That is, the anticancer agent of the present invention may contain an extract from an arctigenin-containing plant, for example, a Burdock Fruit extract obtained from Burdock Fruit, which may further contain arctiin contained in the Burdock Fruit extract.

The anticancer agent of the present invention may contain arctigenin and arctiin so that the weight ratio of arctigenin/arctiin is 0.7 or more. The weight ratio of arctigenin/arctiin may be, but not limited to, 1.3 or less. The anticancer agent of the present invention may contain arctigenin and arctiin as a plant extract which contains arctigenin/arctiin at a weight ratio of 0.7 to 1.3, for example, as a Burdock Fruit extract. In addition, the anticancer agent of the present invention may contain a Burdock Fruit extract which contains 3% or more of arctigenin. Such a Burdock Fruit extract can be obtained according to the process for producing a Burdock Fruit extract as mentioned below. The anticancer agent of the present invention, since it contains a Burdock Fruit extract obtained according to the process for producing a Burdock Fruit extract as mentioned below, shows much higher anticancer effect than those containing a known Burdock Fruit extract.

The anticancer agent of the present invention may further contain any component or components. For example, the anticancer agent of the present invention may be provided in a shape containing pharmaceutically acceptable bases, carriers, diluents, binders, disintegrating agent, lubricants and coloring agents.

The carriers and diluents used in the anticancer agent include, for example, lactose, glucose, white soft sugar, mannitol, dextrin, potato starch, corn starch, calcium carbonate, calcium phosphate, calcium sulfate and crystalline cellulose.

In addition, the binders include, for example, starch, gelatin, syrup, tragacanth gum, polyvinyl alcohol, polyvinyl ether, polyvinylpyrrolidone, hydroxypropylcellulose, methylcellulose, ethylcellulose and carboxymethylcellulose.

In addition, the disintegrating agent include, for example, starch, agar, gelatin powder, crystalline cellulose, calcium carbonate, sodium hydrogen carbonate, sodium alginate, sodium carboxymethylcellulose and calcium carboxymethylcellulose.

In addition, the lubricants include, for example, magnesium stearate, hydrogenated vegetable oil, talc and macrogol. In addition, as for the coloring agent any coloring agents which have been approved to be added to pharmaceutical products can be used.

In addition, the anticancer agent, if required, may be coated with one or more layers such as white soft sugar, gelatin, refined shellac, gelatin, glycerin, sorbitol, ethylcellulose, hydroxypropylcellulose, hydroxypropylmethylcellulose, polyvinylpyrrolidone, phthalic acid cellulose acetate, hydroxypropylmethylcellulose phthalate, methyl methacrylate and methacrylic acid polymer.

In the anticancer agent, if required, a pH-controller, buffering agent, stabilizer and solubilizing agent may be added.

In addition, the anticancer agent can be provided as a pharmaceutical preparation in any forms. For example, the anticancer agent as a preparation for oral administration can be formulated into tablets such as sugar coated tablets, buccal tablets, coating tablets and chewable tablets; troches, pills, powders, capsules including soft capsules, granules, suspensions, emulsions, syrups including dry syrups, as well as liquids and solutions such as elixirs.

In addition, the anticancer agent as a parenteral preparation can be formulated into intravenous injection, subcutaneous injection, intraperitoneal injection, intra-muscular injection, percutaneous preparation, nasal preparation, transpulmonary preparation, enteral preparation, buccal preparation and transmucosal preparation. For example, it may be an injection, transdermal absorbing tape, aerosol preparation and suppositories. In addition, when an extract from a plant is used, it can be a masked preparation or a film coating preparation coated with a protective, since the extract has a peculiar acrid taste.

The anticancer agent of the present invention can be a combination drug mixed with arctigenin and a component having an anticancer activity, or it may be a kit combining the preparations containing the respective components.

When the anticancer agent of the present invention is the combination drug, arctigenin and a component having an anticancer activity can be formulated into a combination drug according to a conventional process for preparing a combination drug by mixing multiple drugs. The combination drug may contain additionally a component or any components other than arctigenin and the component having an anticancer activity. As for the any components, any components included in the above described anticancer agents may be used. The form of the combination drug may be in any forms such as liquid, solid, semisolid and powder. The combination ratio of arctigenin to a component having an anticancer activity can be set in an appropriate combination ratio which can exhibit their respective effects.

When the anticancer agent of the present invention is in a form of kit including a pharmaceutical preparation of arctigenin and a pharmaceutical preparation of a component having an anticancer activity, the pharmaceutical preparation of arctigenin may be in the same form as or in a form different from the pharmaceutical preparation of a component having an anticancer activity. The pharmaceutical preparation of arctigenin and the pharmaceutical preparation of a component having an anticancer activity may be in the same as or different from each other in a way of administration. For example, the pharmaceutical preparation of arctigenin and the pharmaceutical preparation of a component having an anticancer activity both may be administered as an orally administrable preparation or as a parenteral preparation. Alternatively, the pharmaceutical preparation of arctigenin may be administered as an oral preparation and, on the other hand, the pharmaceutical preparation of a component having an anticancer activity may be administered as a parenteral preparation.

The pharmaceutical preparation of arctigenin and the pharmaceutical preparation of a component having an anticancer activity may additionally contain an optional component or components other than arctigenin and the component having an anticancer activity. As for the optional component(s), any component which can be included in the above described anticancer agent may be used.

In Test Examples 1 and 2 as described below, when arctigenin was administered in combination with an existing component having an anticancer activity, it was shown that the proportion of the cancer stem cells in tumor was reduced in comparison with a case where the component having an anticancer activity was administered alone. In Test Example 3 as described below, when arctigenin was administered combined with an existing component having an anticancer activity, it was shown that the side effect was alleviated which had occurred in the separate administration of the component having an anticancer activity. Therefore, the anticancer agent of the present invention exhibits a higher anticancer activity and further it is possible to alleviate the side effect caused by the component having an anticancer activity.

The anticancer agent of the present invention, since it suppresses the growth of tumor and reduces the proportion of the cancer stem cells in tumor, can be used as a agent for curing or improving cancers. The anticancer agent of the present invention can be applied to any type of cancers as therapeutic target depending on the employed component having an anticancer activity. For example, when gemcitabine is used as a component having an anticancer activity, it can be used as a pharmaceutical for curing or improving pancreas cancer, and when bevacizumab (Avastin) is used as a component having an anticancer activity, it can be used as a pharmaceutical for curing or improving colorectal cancer.

[Pharmaceutical Preparation for Combined Administration]

The present invention involves a pharmaceutical preparation for combined administration of arctigenin as an active component in combination with a component having anticancer activity other than arctigenin. The pharmaceutical preparation of the present invention may be in the same composition as the preparation containing arctigenin explained in the anticancer agent as described above. This preparation, for example, may be used as a part of the anticancer agent as described above.

As to the component having an anticancer activity used in combination with the pharmaceutical preparation, the component having an anticancer activity described in the anticancer agent as described above, for example, the existing anticancer agent may be used.

The pharmaceutical preparation of the present invention, when administered in combination with a component having an anticancer activity other than arctigenin, exhibits a higher anticancer effect than arctigenin or the component having anticancer activity which is administered alone, and the side effect caused by the component having an anticancer activity is alleviated.

The pharmaceutical preparation of the present invention may be in a form of sick meal, health food, functional food, food for specified health use, nutritional supplementary food and supplements.

The pharmaceutical preparation of the present invention may be used in an intact form of the powdered extract which is obtained according to a process for producing the Burdock Fruit extract as described below.

[Side Effect-Alleviating Agents]

The present invention further includes a side effect-alleviating agent for reducing side effects caused by the component having an anticancer activity other than arctigenin. The side effect-alleviating agent of the present invention contains arctigenin as active component. The side effect-alleviating agent of the present invention may be used in the same form, dose and dosage regimen as that of the pharmaceutical preparation containing arctigenin as explained in the anticancer agent as described above, in its . The side effect-alleviating agent of the present invention may be made into a combination drug by mixing with a component having an anticancer activity.

The side effect-alleviating agent of the present invention can reduce the side effects caused by the component having an anticancer activity by concomitantly administering as a combination drug with a component having an anticancer activity other than arctigenin. The component having an anticancer activity includes those having anticancer activity as described in the anticancer agents as described above, for example, existing anticancer agents. The side effects include those as described in the above described anticancer agents, particularly myeloid suppression and organ damage.

[Agents for Normalizing Intra-Tumor Blood Vessels]

The present invention also includes an agent for normalizing intra-tumor blood vessels which agent normalizes the blood vessels in tumors.

In this specification, the term "tumor" or "tumor tissue" means a cell group which is constituted by aggregating the plural number of tumor cells, for example, the tissue masses formed by the growth of tumor cells. In this specification, the phrase "normalize the blood vessels in tumor" means that the blood stream in tumor is improved or normalized by suppressing the generation of immature blood vessels formed in tumor tissues. The immature blood vessels in tumor tissues are formed by angiogenesis which is induced by an angiogenic factor released from tumor cells or interstitial cells under hypoxia or undernutrition. Generation of immature blood vessels leads the tumor tissues to circulatory failure, resulting in hypoxia and undernutrition to make delivery of the anticancer agent worse.

The agent for normalizing the intra-tumor vessels in the present invention reduces the tumor tissue under hypoxia and undernutritional environment to suppress the angiogenesis in tumor, and suppress the generation of immature blood vessels to improve the blood stream in the tumor tissue. In addition, the agent for normalizing the intra-tumor vessels in the present invention, as it improves the blood stream in the tumor tissue, can deliver sufficiently an anticancer agent and the like into tumor.

The agent for normalizing the intra-tumor vessels in the present invention contains arctigenin as an active component. The agent for normalizing the intra-tumor vessels in the present invention may be used in the same form, dose and dosage regimen as that of the pharmaceutical preparation containing arctigenin as described in the anticancer agent as described above. In addition, the agent for normalizing the intra-tumor vessels in the present invention may be made into a combination drug by mixing with a component having an anticancer activity.

The agent for normalizing the intra-tumor vessels in the present invention can improve the blood stream in tumor by administering as a combination drug with a component having an anticancer activity other than arctigenin, resulting in enhancing the delivery of the component having an anticancer activity to tumor tissue. The component having an anticancer activity includes those having anticancer activity as described in the anticancer agents as described above, for example, existing anticancer agents. When the agent for normalizing the intra-tumor vessels in the present invention is administered as a combination drug with an existing anticancer agent, it is possible to increase the anticancer effect of the anticancer agent and prolong the survival rate.

[Enhancers of Drug Delivery of Components Having an Anticancer Activity to Tumor Tissue]

The present invention also includes an enhancer of drug delivery of a component having an anticancer activity other than arctigenin to tumor tissue.

In this specification, the term "drug delivery" means the delivery or transfer or transport of a drug to tumor tissue, or incorporation of a drug into tumor tissue.

In this specification, the phrase "enhance the drug delivery" means increase of the amount of drug to be delivered or acceleration of the speed of delivery. The enhancer of the present invention suppresses or removes occurrence of hypoxia and undernutrition in the tumor region where immature blood vessels exist abundantly, while it suppresses generation of new vessels from the existing blood vessels; thus it can improve the blood stream in tumor and enhance the delivery of the agent to tumor tissue. The enhancer of the present invention, when administered combined with an agent, can deliver a larger amount of agent than when the agent is administered alone, or the enhancer can deliver an agent to tumor tissue at a higher rate. The enhancer of the present invention is applicable to increase the incorporation of an agent into tumor tissues.

The enhancer of the present invention contains arctigenin as an active component. The enhancer of the present invention may be used in the same form, dose and dosage regimen as that of the pharmaceutical preparation containing arctigenin as described in the anticancer agent as described above. The enhancer of the present invention may be made into a combination drug by mixing with a component having an anticancer activity.

The enhancer of the present invention, when administered as s combination drug with a component having an anticancer activity other than arctigenin, can increase the delivery of the component having an anticancer activity. The component having an anticancer activity includes those having an anticancer activity as explained in the anticancer agent as described above, for example, existing anticancer agents. The enhancer of the present invention, when administered as a combination drug with an existing anticancer agent, can potentiate the antitumor activity of the anticancer agent and prolong the survival rate.

[Method]

The present invention involves a method for treating, improving or preventing cancer. The method for treating, improving or preventing cancer in the present invention includes a step of administering an effective dose of arctigenin to a target in combination with an effective dose of a component having an anticancer activity other than arctigenin.

The present invention also provides a method for alleviating a side effect. The method for alleviating a side effect in the present invention is for alleviating the side effect caused by a component having an anticancer activity other than arctigenin, and includes a step of administering an effective dose of arctigenin to a subject. In the step of administration in this method for alleviating the side effect, an effective dose of arctigenin may be administered to a subject in combination with a component having an anticancer activity other than arctigenin.

The present invention also involves a method for normalizing the blood vessel in tumor. The method for normalizing the blood vessel in tumor according to the present invention includes a step of administering an effective dose of arctigenin to a subject. In the administration step in the method for normalizing the blood vessel in tumor according to the present invention, an effective dose of arctigenin may be administered to a subject in combination with an effective dose of a component having an anticancer activity other than arctigenin.

The present invention also involves a method for enhancing the drug delivery to tumor tissue of a component having an anticancer activity. The method for enhancing the drug delivery to tumor tissue of a component having an anticancer activity according to the present invention includes a step of administering an effective dose of arctigenin to a subject. In the administration step in the method for enhancing the drug delivery to tumor tissue of a component having an anticancer activity according to the present invention, an effective dose of arctigenin may be administered to a subject in combination with an effective dose of a component having an anticancer activity other than arctigenin.

In the method of the present invention, arctigenin and the component having an anticancer activity other than arctigenin may be made into a combination drug. In the administration step in the method of the present invention, a pharmaceutical preparation of arctigenin and a pharmaceutical preparation of a component having an anticancer activity may be administered separately. In the method of the present invention, arctigenin may be a Burdock Fruit extract.

In the method of the present invention, the effective dose of arctigenin means the dose at which the cancer in the subject of administration is treated, improved or prevented, the dose at which the blood vessels in tumor are normalized, or the dose at which an effective dose of the component having an anticancer activity is delivered to tumor tissue. In addition, the effective dose of the component having an anticancer activity indicates the dose at which the cancer in the target of administration is treated, improved or prevented. In addition, the "target" of administration includes human, non-human mammal and non-mammal.

The way of administration in the method of the present invention includes oral administration and parenteral administration, for example, intravenous injection, subcutaneous injection, intraperitoneal injection, intramuscular injection, transdermal administration, nasal administration, transpulmonary administration, enteral administration, buccal administration and transmucosal administration. In the method of the present invention, arctigenin and a component having anticancer activity may be administered as orally administrable preparations, namely, tablets such as sugar coated tablets, buccal tablets, coating tablets and chewable tablets, troches, pills, powders and soft capsules including capsules, granules, suspensions, emulsions, syrups including dry syrups, as well as liquids such as elixirs. In addition, in the method of the present invention, arctigenin and a component having anticancer activity may be administered as parenterally administrable preparations, for example, injections, transdermal absorbing tapes, aerosol preparations and suppositories.

In the method of the present invention, arctigenin and a component having anticancer activity may be administered at an optional dose, for example, at a single dose or multiple doses that are usually employed in Chinese medicines or anticancer agents. For example, arctigenin employed in the method of the present invention may be administered at a dose of 10 to 2,000 mg a day for an adult. The component having an anticancer activity may be also administered at a dose at which the anticancer activity is generated. For example, when the component having an anticancer activity is gemcitabine, it may be administered at a dose of 500 to 2,000 mg/mm$^2$ a day. When the component having an anticancer activity is bevacizumab (Avastin etc.), it may be administered at a dose of 5 to 30 mg/kg a day.

[Process for Producing a Burdock Fruit Extract]

The Burdock Fruit extract appropriate for the anticancer agents, pharmaceutical preparations and side effect alleviating agents of the present invention may be produced through the steps of cutting of crude drug, extracting (step of conversion by an enzyme and step of extraction with an organic solvent), solid-liquid separating, concentrating and drying.

[Step of Cutting of Crude Drug]

In the cutting step for crude drug, Burdock Fruit as raw material is cut into an appropriate size for extraction. The crude drug as raw material has a variety of size, shape, and hardness according to the various parts of plants, minerals or animals, and appropriate cutting is necessary according to its quality. Burdock Fruit can be cut by an optional means well-known to a person skilled in the art. For example, a commercially available cutter may be used.

In the process for producing a Burdock Fruit extract suitable to the present invention, the β-glucosidase activity resulting from the enzyme existing in Burdock Fruit is determined in advance to select suitable Burdock Fruit. In a method for determining the β-glucosidase activity, for example, p-nitrophenyl-β-D-glucopyranoside ($C_{12}H_{15}NO_8$: molecular weight 301.25) (by SIGMA-ALDRICH CO.) is used as a substrate, which is made act on the pulverized product of Burdock Fruit to yield p-nitrophenol, and the variation of absorbance at 400 nm of it is measured to determine the enzyme activity. The enzyme activity may be defined as the amount of enzyme which yields 1 micromole of p-nitrophenol for 1 minute is 1 unit (U).

In order to obtain a Burdock Fruit extract suitable for the present invention, Burdock Fruit which has for example 0.4 U/g or more, preferably 1 U/g or more of the β-glucosidase activity existing in Burdock Fruit can be used. When the enzyme activity is less than 0.4 U/g, the hydrolysis results in insufficiency, the weight proportion of arctigenin is decreased and a desired Burdock Fruit extract is unable to obtain efficiently.

In a method for producing a Burdock Fruit extract suitable for the present invention, it is possible to use Burdock Fruit cut into an optional grain size. It is considered that the smaller the grain size of cut Burdock Fruit is, the more the enzymatic conversion is promoted, and the more the yield of extraction is increased. On the other hand, when the grain size is too small, the process control becomes difficult because the enzymatic conversion is too fast, or the exact solid-liquid separation runs into trouble in the following step in some cases.

In order to obtain a Burdock Fruit extract suitable for the present invention, Burdock Fruit is cut into grain size of 9.5 mm or less as shown in Example below, for example, so that the grain entirely passes through a screen of 9.5 mm. In addition, in order to obtain a Burdock Fruit extract suitable for the present invention, it is desirable to cut Burdock Fruit so that the grain size of Burdock Fruit entirely passes through a screen of 9.5 mm, for example, 60 to 100% is distributed on a screen of 0.85 mm, more preferably 65 to 80% is distributed on a screen of 0.85 mm.

(Extraction Step)

The extraction step is the most important step in quality control in the process for producing the extracted and pulverized products from crude drugs. The quality of the extracted and pulverized products from crude drugs is determined by this extraction step. In a process for producing a Burdock Fruit extract suitable for use in the anticancer agent of the present invention, the extraction is carried out in 2 steps, that is, the step of enzymatic conversion and the step of extraction with an organic solvent.

(Step of Enzymatic Conversion)

The step of enzymatic conversion is an important step in the process for producing a Burdock Fruit extract suitable for the present invention. In the step of enzymatic conversion, arctiin contained in Burdock Fruit is enzymatically converted into arctigenin by β-glucosidase, an enzyme existing in Burdock Fruit.

Specifically, the cut product of Burdock Fruit provided in the above described steps is kept at an appropriate temperature so that β-glucosidase acts thereon to make the reaction of arctiin to arctigenin proceed. For example, an optional solution such as water is added to the cut product of Burdock Fruit and stirred at a temperature around 30° C. to keep Burdock Fruit at an optional temperature.

In order to obtain a Burdock Fruit extract suitable for the present invention, the cut product of Burdock Fruit is kept at a temperature around 30° C., for example at a temperature between 20 and 50° C. In a case at lower than 20° C., it is not possible to obtain the desired extract of Burdock Fruit efficiently since the hydrolysis is insufficient to decrease the weight ratio of arctigenin. On the other hand, in a case at higher than 50° C., it is not possible to obtain the desired extract of Burdock Fruit efficiently since the enzyme is inactivated to decrease the weight ratio of arctigenin.

There is no particular limitation in retention time as far as the above described temperature is kept, for example, it may be kept for about 30 minutes. When the temperature is kept between 20 and 50° C., an appropriate amount of arctiin is enzymatically converted into arctigenin irrespective of the retention time to yield a Burdock Fruit extract suitable for the present invention.

[Step of Extraction with an Organic Solvent]

In the step of extraction with an organic solvent, arctigenin and arctiin are extracted from Burdock Fruit with an optional and appropriate organic solvent. Namely, when the step of enzymatic conversion as described above reaches an arctigenin rich state, an appropriate solvent is added thereto to extract a Burdock Fruit extract. For example, an appropriate solvent is added to a Burdock Fruit extract and stirred under heating for an appropriate period of time to extract a Burdock Fruit extract. Besides the stirring under heating, the other optional extraction method well-known to a person skilled in the art such as reflux under heating, drip-type extraction, immersion-type extraction or pressure-type extraction may be applied to extract a Burdock Fruit extract.

Since arctigenin is slightly soluble in water, it is possible to improve the yield of arctigenin by means of addition of an organic solvent. As for organic solvents, an optional organic solvent may be used. For example, an alcohol such as methanol, ethanol and propanol, as well as acetone may be used. In view of the safety, it is appropriate to use ethanol as an organic solvent in the process for producing a Burdock Fruit extract suitable for the present invention.

When a Burdock Fruit extract is extracted by heating under stirring, the temperature is kept at 80° C. or higher, for example, between 80 and 90° C., in order to obtain a Burdock Fruit extract suitable for the present invention, though the heating under stirring may be carried out at an optional temperature. In addition, there is no particular limitation in the time for heating under stirring as far as the heating under stirring is conducted at the temperature as described above; thus, arctigenin and arctiin can be extracted from Burdock Fruit into a solvent by heating under stirring for about 30 minutes, for example, 30 to 60 minutes. The longer the time of heating under stirring is, the higher the yield of arctigenin and arctiin is enhanced. The longer time of heating under stirring, however, abundantly elutes unnecessary oils and fats, resulting in increase of the burden in the concentration step. Therefore, the time of heating under stirring may be determined according to the situation.

The yield of arctigenin and arctiin is raised along with increase of the amount of ethanol since the solubility of arctigenin and arctiin become higher. However, an excess amount of ethanol elutes a large quantity of oils and fats unnecessarily and increases the burden in the concentration step. The amount to be added may be determined according to the situation. In this connection, the heating with stirring in this step is accompanied by sterilization and pasteurization of the Burdock Fruit extract concurrently.

(Step of Solid-Liquid Separation)

In the step of solid-liquid separation, Burdock Fruit after completion of extraction is separated from the extract. The solid-liquid separation may be carried out according to an optional conventional manner well-known by a person skilled in the art. The method of solid-liquid separation includes methods of filtration, methods of sedimentation and methods of centrifugal separation. Industrially, it is desirable to use a method of centrifugal separation.

(Step of Concentration)

In the step of concentration, the solvent is removed from the Burdock Fruit extract prior to drying. Removal of the solvent from the Burdock Fruit extract may be conducted according to a conventional optional manner well-known to a person skilled in the art. In this step, however, it is desirable to avoid that the Burdock Fruit extract obtained in the above described step is exposed to a higher temperature for a long period of time. For example, it is possible to concentrate the Burdock Fruit extract without exposing it at high temperatures for a long period of time by employing a method for concentrating under reduced pressure.

Concentration of the Burdock Fruit extract may be conducted until the Burdock Fruit extract reaches the desired concentration. For example, it is desirable to conduct the concentration to the extent that the drying operation can be achieved appropriately in the following step of drying. Further, it is desirable to conduct the concentration so that the concentrate affords an appropriate character of pharmaceutical preparation when the Burdock Fruit extract is dried to yield a powder preparation in the following step.

Since arctigenin and arctiin are slightly soluble in water, they adhere abundantly to the inside of a manufacturing apparatus in the following drying step to greatly lower the final yield. In order to prevent the adhesion of arctigenin and arctiin, it is possible to add dextrin to the Burdock Fruit extract obtained in the concentration step. Dextrin may be added desirably in an amount of about 15 to 30% for the solid potion of concentrated solution.

(Drying Step)

In this step, the Burdock Fruit extract obtained in the above described step is finished in powder. Drying may be carried out according to a conventional any method well-known to a person skilled in the art. For example, freeze-drying and spray drying have been known as drying methods, and in general the former is employed at a laboratory level and the latter at a level of the large scale production.

According to the above described production steps, a Burdock Fruit extract containing a large quantity of arctigenin can be obtained. In this process for producing a Burdock Fruit extract, it is necessary to include the step for conducting an enzymatic conversion reaction at a temperature of 20° C. to 50° C., though all of the other steps are not always required.

According to the above described production steps, a Burdock Fruit extract containing a high concentration of arctigenin can be obtained inexpensively and conveniently. Therefore, the anticancer agent, pharmaceutical preparation and side-effect alleviating agent can be obtained inexpensively and conveniently by using a Burdock Fruit extract obtained in this method.

Since the Burdock Fruit extract obtained in the above described production steps has a high arctigenin concentration, it is possible to reduce the total amount per day in the anticancer agent, pharmaceutical preparation and side-effect alleviating agent compared with a case where the usual Burdock Fruit extract is used. Therefore, the burden imposed on patients can be relieved.

EXAMPLES

Example 1

According to the following method, a Burdock Fruit extract containing arctigenin was prepared.

Burdock Fruit (enzyme activity: 7.82 U/g) was cut, and those which passed entirely through a 9.5 mm screen were further passed through a 0.85 mm screen, 75% of them were confirmed to remain thereon. The finely cut Burdock Fruit (80 kg) was added into 560 L of water warmed at 30 to 32° C., which was added to 253 L of ethanol, and the mixture was heated up at 85° C. and refluxed under heating for 40 minutes. The solution was subjected to centrifugal separation and yielded an extract. This operation was repeated twice, and the combined extracts were concentrated under reduced pressure to yield a solid content, which was added to 25% of dextrin followed by spray drying. The contents of arctigenin and arctiin were 6.4% and 7.2% respectively, Burdock Fruit extract powder (containing 25% of dextrin) of the ratio of arctigenin/arctiin (weight ratio)=0.89 was obtained.

Test Example 1

Burdock Fruit extract containing arctigenin, bevacizumab and gemcitabine were repeatedly administered to evaluate the blood stream in tumor. Avastin was used as bevacizumab.

Human pancreatic cancer cell Suit 2 ($1 \times 10^6$ cells) was transplanted subcutaneously to BALB/cAJc1-nu/nu mice (CLEA Japan, Inc.). On 21th day after the transplantation, the transplanted mice were divided into 4 groups, that is, (a) an untreated group, (b) a group to which a Burdock Fruit extract was administered, (c) a group to which bevacizumab was administered, and (d) a group to which gemcitabine was administered, and the treatment was continued for 4 weeks. The Burdock Fruit extract of Example 1 was mixed into feed at a rate of 0.5% (w/w) and the resultant was given to mice. The ingestion of feed was 3 to 5 g a day for a mouse, from which the intake of arctigenin was calculated as 15 to 25 mg/mouse/day. Bevacizumab, as Avastin 100 mg/4 ml for intravenous injection (Chugai Pharm. Co.), was intraperitoneally injected at a dose of 5 mg/kg once a week. As gemcitabine, an intravenous drip preparation of gemcitabine (Eli Lilly and Co.) was intraperitoneally injected at a dose of 100 mg/kg twice a week.

(Tumor Size)

The average tumor size after 4 weeks from the starting of treatment in the respective groups was as follows: (a) 228 mm$^2$ in the untreated group; (b) 189 mm$^2$ in the Burdock Fruit extract administered group; (c) 56 mm$^2$ in the bevacizumab administered group to which was; and (d) 68 mm$^2$ in the gemcitabine administered group.

(Uptake of Gadolinium DTPA in Tumor Tissue)

After 4 weeks from the starting of treatment, the uptake of gadolinium DTPA in the mouse tumor tissue was evaluated in the respective groups. Up to 120 seconds after rapid intravenous injection of gadolinium DTPA, a dynamic imaging $T_1$-weighted image (time resolution: 1.8 to 5.3 sec) was photographed using a 9.4 tesla MRI apparatus (BIOSPEC 94/20USR). From this photograph the signal intensity of gadolinium DTPA in the tumor tissue was measured. FIG. 1 is a graph showing the average values of signal intensity every 30 seconds, when the signal intensity at 0 second after intravenous injection of gadolinium DTPA was regarded as 100. Increase of the signal intensity of gadolinium DTPA in the tumor tissue indicates the uptake of gadolinium DTPA into the tumor tissue. The degree of the uptake of gadolinium DTPA into the tumor tissue is an indicator of the state of blood stream in the tumor tissue.

(Evaluation of Blood Stream in the Tumor Tissue after Treatment)

As shown in FIG. 1, during a period of 90 to 120 seconds after the treatment by intravenous injection of gadolinium DTPA, the signal intensity in the central part of tumor tissue increased up to 118.1±13.7% in the group administered the Burdock Fruit extract. On the other hand, in the untreated group, it was 102.6±3.4% during a period of 90 to 120 seconds, indicating that there was no increase. Accordingly, the blood stream in the group administered the Burdock Fruit extract had better tendency (P<0.05, t-test) compared with the untreated group. In the gemcitabine-treated group which showed the antitumor activity, no increase was recognized in the signal intensity in the central part of tumor tissue similarly in the untreated group. On the other hand, in the group treated with bevacizumab having an angiogenesis-inhibiting activity, a tendency of increasing the signal intensity was seen.

The above results have suggested a possibility that the administration of a Burdock Fruit extract containing arctigenin reduces a region poor in blood stream and keeps a region rich in blood stream. Accordingly, it is suggested that the administration of arctigenin regulates to arrange the environment so that drugs are delivered easily to tumor tissue. Therefore, it is suggested that the drug delivery of anticancer agents to tumor tissue is enhanced, and as a result the drug effect is enhanced.

Test Example 2

In the course of the growth of tumor, nutrition and oxygen have to be supplied over the grown entire tumor tissue through the blood vessels. In most of tumor, however, it is considered that these are not supplied sufficiently because of immature angioplasty to cause a partial necrosis of tissue and an ulcerous portion occurs. In this situation, in order to inspect the effect of normalization of intra-tumor blood stream by the above described Burdock Fruit extract, the occurrence of ulcer in the tumor tissue after the respective treatments was observed.

(Ulceration)

Figure 2:
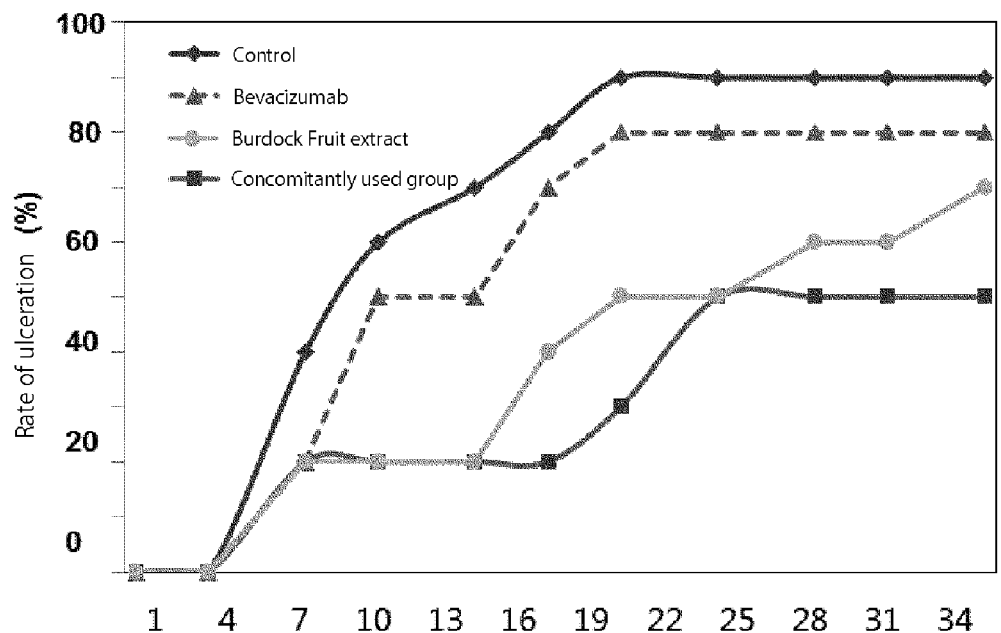
FIG. 2 shows the frequency of occurrence of intra-tumor ulcer tissues after administration of the concomitant preparation according to the embodiment of the present invention.

For tumor tissue, a single administration of a Burdock Fruit extract, a single administration of bevacizumab and a combined administration of a Burdock Fruit extract and bevacizumab were performed over a period of 5 weeks. FIG. 2 shows the rate (%) of mice which generated the ulcer in the tumor is for an untreated group (Control) and the respectively administered groups. As shown in FIG. 2, the duration until the generation of ulcer reached 50% was 8 days in the untreated group, 20 days in the Burdock Fruit extract-administered group, 10 days in the bevacizumab-administered group, and 24 days in the concomitantly administered group. Thus, the suppression effect on ulcer generation in tumor was recognized in the Burdock Fruit extract-administered group and the concomitantly administered group compared with that in the untreated group and the bevacizumab-administered group. In the bevacizumab-administered group, the inhibitory effect for ulcer generation was recognized in comparison with the untreated group, though it was temporal. This effect is considered to be an inhibitory activity of bevacizumab for angiogenesis. On the other hand, when the combined administration of a Burdock Fruit extract in addition to bevacizumab, the inhibitory effect on ulcer generation was raised. This is considered that, in addition to the improved effect for blood stream in tumor by a single preparation of bevacizumab, the blood stream was further improved by combined administration of a Burdock Fruit extract which suppressed an occurrence of a hypoxia and undernutritional region and further suppressed angiogenesis. Thus, since the combined administration of arctigenin can markedly reduce a hypoxia and undernutritional region, it is expected to suppress the malignant transformation of cancer.

(Life Prolongation by Concomitant Use)

Figure 3:
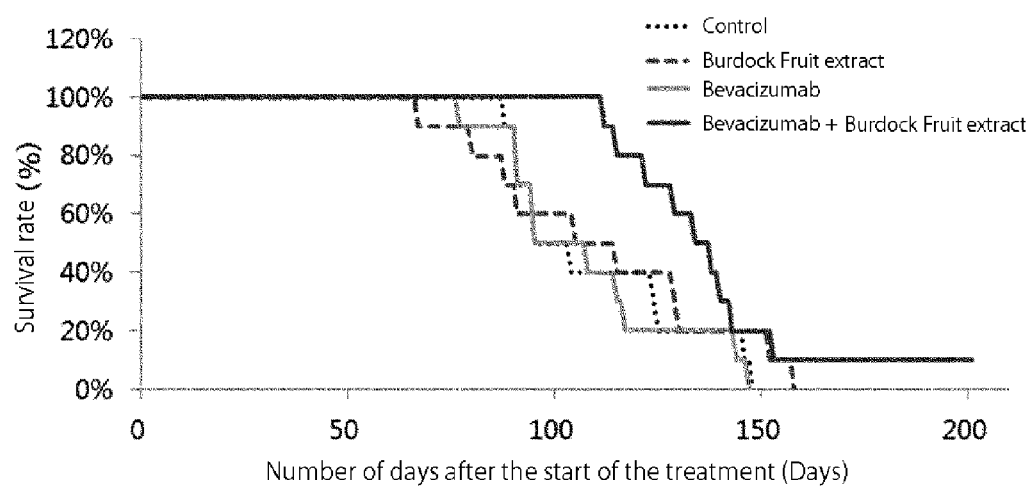
FIG. 3 shows the survival rate after administration of the concomitant preparation according to the embodiment of the present invention.

Therapeutic treatment was terminated after it was continued for 5 weeks, and the survival period was followed up. FIG. 3 shows the survival rate of the respective groups. The results were as follows as shown in FIG. 3; the 50% survival period was 103 days in the untreated group, 114 days in the Burdock Fruit extract-administered group, 107 day in the bevacizumab-administered group, and 137 days in the concomitantly administered group. Accordingly, the life prolongation in the group of the combined administration was estimated to be 33% and 20-28% respectively compared with those of the untreated group and the single administration group.

Test Example 3

The antitumor effect by the combined administration of a Burdock Fruit extract and gemcitabine was examined.

(Preparation of Mice Transplanted Human Pancreatic Cancer Cell)

Human pancreatic cancer cells Miapaca-2 (ATCC CRL 1420) (5×10$^6$ cells/200 μl) were transplanted subcutaneously under the armpit of BALB/cAJcl nu/nu mice (CLEA Japan, Inc.). After feeding for about 2-3 weeks, those of which cancer grew to about 100 mm$^3$ were selected and employed as the subject mice to be treated.

(Therapeutic Test for Pancreatic Cancer)

The subject mice of treatment were divided into 4 groups, that is, (a) an untreated group, (b) a group administered gemcitabine, (c) a group administered a Burdock Fruit extract, and (d) a group administered in combination with a Burdock Fruit extract and gemcitabine (combined administration group), and the treatment was continued for 4 weeks. The Burdock Fruit extract, 250 mg/kg prepared in Example 1 (25 mg/kg or more as arctigenin), was orally administered everyday (for 5 times a week). As gemcitabine, an intravenous drip preparation of gemcitabine (Eli Lilly and Co.) was used, and 150 mg/kg was intraperitoneally given twice a week.

(Tumor Weight)

After termination of the therapeutic test, the tumor weight was measured in the respective groups. As results, the tumor weight after termination of the therapeutic test was as follows: 2.05 g in the untreated group, 1.24 g in the gemcitabine-administered group, 0.98 g in the Burdock Fruit extract-administered group, and 0.82 g in the concomitantly administered group. Accordingly, in any group including the gemcitabine-administered group, the Burdock Fruit extract-administered group and the concomitantly administered group, the suppression of tumor weight was recognized in the degree of about 40 to 60% compared with the untreated group.

(Proportion of the Cancer Stem Cells in Tumor)

The cancer cells were recovered from the tumor tissue after termination of the treatment test, and using the triple positive markers, CD24, CD44 and ESA (CD326) as well as the double positive markers, CD133 and CD44, and the proportion of $CD44^+$, $CD24^+$, $CD326^+$ cells (triple positive) and $CD133^+$, $CD44^+$ cells (double positive) was evaluated. In the evaluation, a FACS ARIA II flow cytometer (BD bioscience) was used. The $CD44^+$, $CD24^+$, $CD326^+$ cells (triple positive) are cancer stem cells superior in tumorigenicity, and the $CD133^+$, $CD44^+$ cells (double positive) are extremely highly metastatic cancer stem cells. The proportion was determined as follows; the cells existing in tumor was treated with TruStain fcX (mouse, biolegend), and the dead cells were eliminated with Sytox-Red (Invitrogen) and the cells of mouse origin was eliminated with a mouse lineage cocktail (biolegend), anti-H2-Kd (biolegend) to give the proportion in the remaining pancreatic cancer cells ($2.5 \times 10^4$).

Figure 4:
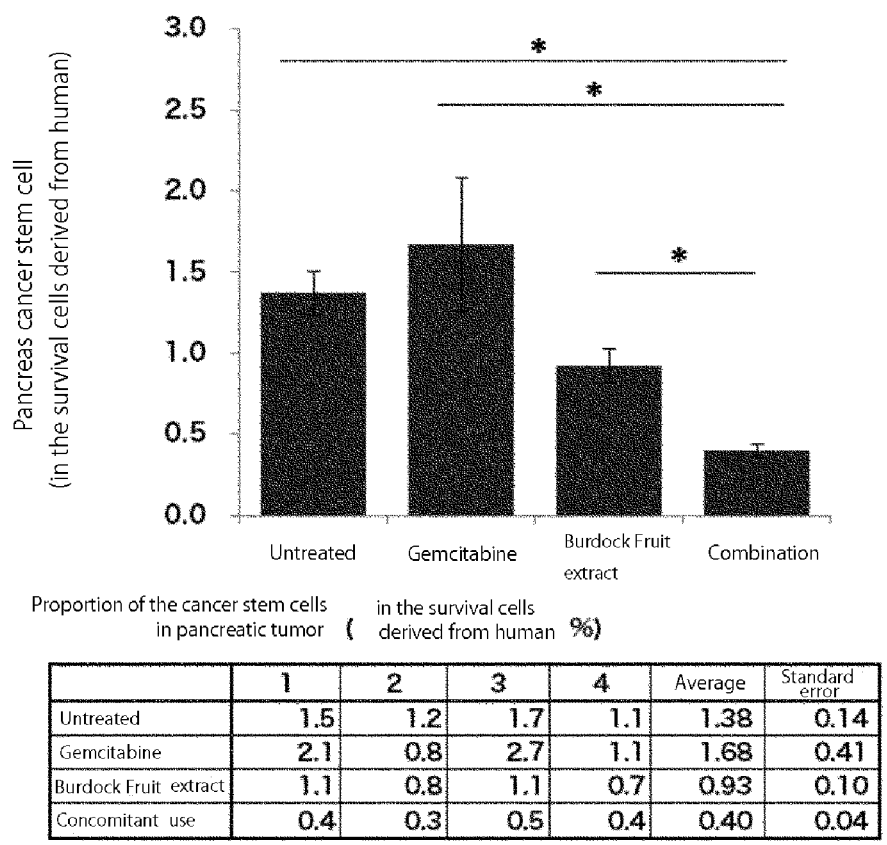
FIG. 4 shows the result of evaluation on the proportion of intra-tumor $CD44^+$, $CD24^+$ and $CD326^+$ cells (triple positive) after administration of the concomitant preparation according to the embodiment of the present invention.

FIG. 4 shows the results of evaluation from the ratio of $CD44^+$, $CD24^+$, $CD326^+$ cells (triple positive) in tumor after the therapeutic test. In Table under FIG. 4, the respective ratios in 4 test samples and the average values are shown. As a result, the ratio of $CD44^+$, $CD24^+$, $CD326^+$ cells (triple positive) was as follows: 1.4% in the untreated group, 1.6% in the gemcitabine-administered group, 1.0% in the Burdock Fruit extract-administered group, and 0.4% in the combined administration group. Thus, in the group of the combined administration of Burdock Fruit extract and gemcitabine, it was recognized that the ratio of the triple positive cancer stem cells in tumor significantly lowered in comparison with those of the untreated group and the single administration group.

In addition, the ratio of the $CD133^+$, $CD44^+$ cells (double positive) in tumor after termination of the therapeutic test was evaluated; the results were as follows: 2.3% in the untreated group, 3.5% in the gemcitabine-administered group, 1.7% in the Burdock Fruit extract-administered group, and 0.5% in the combined administration group. Thus, in the double positive cancer stem cells, it was recognized that the ratio in tumor lowered in the combined administration group compared to those of the untreated group and the single administration group.

From these results, it was elucidated that the combination of a Burdock Fruit extract and gemcitabine can suppress the growth of tumor and reduce the ratio of pancreatic cancer stem cells in tumor which possibly causes the recurrence of tumor, distant metastasis and the occurrence of resistance to anticancer agents. Accordingly, it was shown that a concomitant preparation of Burdock Fruit extract and gemcitabine exhibits a remarkably higher anticancer activity than that expected from the single administration of the respective ones.

Test Example 4

The 5 years survival rate of pancreas cancer after the diagnosis was lower than 5% at a point in 2013, and the average survival period was limited to only 4 to 6 months. These values are extremely lower than those of other cancers, requiring effective measures. In Example 3 as described above, there was recognized a tendency that a combined treatment with a Burdock Fruit extract rich in arctigenin and gemcitabine suppressed the growth of tumor compared with the single treatment in a model which was transplanted pancreatic tumor. In such a situation, an orthotopic graft model into mouse pancreas was prepared as a model similar to an actual nidus, and the influence on the survival rate which was brought about by concomitant treatment with gemcitabine and a Burdock Fruit extract was evaluated.

(Preparation of an Orthotopic Graft Model of Pancreas Cancer)

Human pancreas cancer cells Miapaca-2 cells were suspended in a highly concentrated Matrigel solution (BD bioscience) at $5 \times 10^6$ cells/50 µl. A female BALB/cAJcl-nu/nu mice (8 weeks of age) (CLEA Japan, Inc.) were subjected to laparotomy under anesthesia, the above-prepared cell suspension was poured into pancreatic tissue and solidified, followed by suture and closing.

(Treatment)

The mice after transplantation were divided into 4 groups (7 mice in one group), that is, an untreated group (Non treat); a group to which 250 mg/kg of Burdock Fruit extract (Kracie Pharm., GBS-01) containing 10% of arctigenin was orally administered every day (GBS-01); a group which was intraperitoneally given 150 mg/kg of gemcitabine (Eli Lilly & Co.) twice a week (Gemcitabine); and a group of combined administration of them(Combination), and the treatment was continued until all of the mice died.

(Analysis of Survival Rate)

The survival rate was calculated according to the Kaplan-Mayer method by making a curve of survival rate and calculating the median of survival rate (MST) (GraphPad-PRISM 6.2, MDF Co.). The significant difference was evaluated by means of Logrank (Mantel-COX) and Gehan-Breslow-Wilcoxon test. The calculated results were shown on an upper graph of FIG. 5.

As shown in FIG. 5, the median of survival time (MST) was respectively as follows: 65 days in the untreated group (Non treat); 86 days (prolongation of 32.3%) in the gemcitabine administered group (Gemcitabine); 88 days (prolongation of 35.4%) in the Burdock Fruit extract administered group (GBS-01); and 117 days (prolongation of 80%) in the concomitant treatment (Combination). The significant differences in the treated group and the untreated group were recognized both in the Gehan-Breslow-Wilcoxon test and the Log-RANK (Mantel-Cox) test.

As a result, in the orthotopic graft model of pancreas cancer, as shown in FIG. 5, compared with the untreated group, the Burdock Fruit extract (GBS-01) group and the gemcitabine administered group (Gemcitabine) showed approximately the same level of life prolongation. On the other hand, in the combined administration group (Combination) which were combined these drugs, a remarkable life prolongation was shown compared with that of the untreated group and the single administration groups. Accordingly, it was shown that the combined administration of an anticancer agent and arctigenin can extend greatly the life prolongation even in pancreas cancer which is very difficult to extend the survival period.

Test Example 5

As for a variety of drugs which exhibit a damaging activity to cancer cells in diverse mechanisms, a killing activity of these drugs was examined as to an increase of the activity by combined administration of arctigenin derived from Burdock Fruit.

The pancreas cancer cells, PANC-1 (ATCC No. CRL-1469) cells, were treated with a variety of drugs as shown in Table 1 below, arctigenin (refined product, lot: AG-STD1, Kracie, Co.) and their combined preparations (Combination) in a culture medium (DMEM (SIGMA)+5% dialyzed fetal bovine serum+4 mM Glutamine+10 mM HEPES). A variety of drugs were used at a ¼ concentration (killing rate less than 15%) of the 50% lethal concentration ($LD_{50}$). Arctigenin was used in a dilution series up to 1 nM-3000 nM. After treatment for a period of 18-24 hours, the number of survival cells was counted with a Cell Counting Kit (Dojindo).

Table 1 below shows the magnification of $LD_{50}$ lowering for a single drug treatment with arctigenin compared with a case of the combined treatment with a variety of agents and arctigenin. In a variety of drugs, when concomitantly treated with arctigenin, the lowering of $LD_{50}$ was recognized compared with the single treatment with arctigenin and the single treatment with other drugs.

| Drug | Selling Agency | Magnification of LD50 decrease |
| --- | --- | --- |
| AG1024 | ALEXIS | 3.67 |
| AKT inhibitor V | Merck | 4.75 |
| AZT | Wako Pure Chem. | 4.67 |
| Benzylguanine | ALEXIS | 8.24 |
| Damnacanthal | CalbioChem | 1.84 |
| Deprenyl | MBP | 3.21 |
| Deferoxamine mesylate | SIGMA | 6.22 |
| DHEA-S | Tokyo Chemical Ind. Inc. | 3.13 |
| Dorsomorphin | SIGMA | 6.14 |
| Forskorin | Tokyo Chemical Ind. Inc. | 6.17 |
| Fumonisin B1 | SIGMA | 8.04 |
| Gant 61 | Wako Pure Chem. | 7.59 |
| GGTI-286 | CalbioChem | 1.74 |
| hydroxychloroquine | Tokyo Chemical Ind. Inc. | 9.32 |
| L-NMMA | Wako Pure Chem. | 1.72 |
| Lovastatin | Wako Pure Chem. | 1.98 |
| ML-7 | CalbioChem | 7.61 |
| Nutlin-3 | CAYMAN | 5.24 |
| PD173074 | CAYMAN | 5.79 |
| PF-04217903 | SYK | 3.61 |
| Purvalanol A | CalbioChem | 1.71 |
| Radicicol | CalbioChem | 1.81 |
| Ro-20-1724 | CalbioChem | 1.66 |
| Cerulenin | Sigma | 3.10 |
| Sodium salicylate | Wako Pure Chem. | 2.36 |
| SP600125 | TOCRIS | 1.77 |
| Spautin | SIGMA | 6.21 |
| SU1498 | CalbioChem | 2.12 |
| Theophylline | Wako Pure Chem. | 1.75 |
| Troglitazone | CalbioChem | 8.17 |
| AG1024 | ALEXIS | 3.67 |
| AKT inhibitor V | Merck | 4.75 |
| AZT | Wako Pure Chem. | 4.67 |
| Benzylguanine | ALEXIS | 8.24 |
| Damnacanthal | CalbioChem | 1.84 |
| Deprenyl | MBP | 3.21 |
| Deferoxamine mesylate | SIGMA | 6.22 |
| DHEA-S | Tokyo Chemical Ind. Inc. | 3.13 |
| Dorsomorphin | SIGMA | 6.14 |
| Forskorin | Tokyo Chemical Ind. Inc. | 6.17 |
| Fumonisin B1 | SIGMA | 8.04 |
| Gant61 | Wako Pure Chem. | 7.59 |
| GGTI-286 | CalbioChem | 1.74 |
| hydroxychloroquine | Tokyo Chemical Ind. Inc. | 9.32 |
| L-NMMA | Wako Pure Chem. | 1.72 |
| Lovastatin | Wako Pure Chem. | 1.98 |
| ML-7 | CalbioChem | 7.61 |
| Nutlin-3 | CAYMAN | 5.24 |
| PD173074 | CAYMAN | 5.79 |
| PF-04217903 | SYK | 3.61 |
| Purvalanol A | CalbioChem | 1.71 |
| Radicicol | CalbioChem | 1.81 |
| Ro-20-1724 | CalbioChem | 1.66 |
| Cerulenin | Sigma | 3.10 |
| Sodium salicylate | Wako Pure Chem. | 2.36 |
| SP600125 | TOCRIS | 1.77 |
| Spautin | SIGMA | 6.21 |
| SU1498 | CalbioChem | 2.12 |
| Theophylline | Wako Pure Chem. | 1.75 |
| Troglitazone | CalbioChem | 8.17 |

From these results, it has been shown that arctigenin has a broad enhancing activity for agents having a damaging effect to cancer cells in various mechanisms in the treatment of some type of cancers represented by pancreas cancer which readily turns into a starving state for the tumor inside.

Test Example 6

A model which was transplanted pancreas cancer was used and treated with a variety of existing anticancer agents, a Burdock Fruit extract rich in arctigenin and a combination of these drugs, and the variation of the tumor size was evaluated.

(Preparation of a Model Transplanted Pancreas Cancer)

Miapaca-2 cells ($5 \times 10^6$ cells/200 µl) were subcutaneously transplanted under the armpit of BALB/cAJcl-nu/nu mice (CLEA Japan, Inc.), and after feeding of about 2 weeks those that grew to the size of about 100 mm³ or about 600 mm³ were selected and employed as the subject mice to be treated.

(Treatment)

Thus prepared transplanted mice were divided into the respective groups, that is, an untreated group, a group administered an existing anticancer agent as a component having a variety of anticancer activities, a Burdock Fruit extract administered group and a group of combined administration of these agents, and the treatment was continued over about 4 weeks for 5 to 6 species of tumors in the respective groups. The existing anticancer agents used include Carboplatin (CBDCA, Bristol-Myers, peritoneal administration, 60 mg/kg once a week), Doxorubicin (Kyowa Hakko, peritoneal administration, 10 mg/kg twice a week), Oxaliplatin (Yakult, peritoneal administration, 8 mg/kg once a week), Everolimus (Novartis, oral administration, 5 mg/kg 5 times a week), Bortezomib (Janssen Pharma, peritoneal administration, 1 mg/kg twice a week), Irinotecan (Yakult, peritoneal administration, 25 mg/kg twice a week), and Hydroxychloroquine (Sanofi, peritoneal administration, 100 mg/kg 5 times a week). As for Burdock Fruit extract, 10% arctigenin-containing Burdock Fruit extract (Kracie Co., GBS-01) was used and orally administered at a dose of 750 mg/kg 5 days a week.
(Measurement of Tumor Size)

At intervals of 3 to 4 days, the mouse was fixed and the length (L), the minor axis (W) and the height (H) of tumor were measured by a precision digital vernier micrometer, from which the tumor size was calculated using the formula:

Tumor size=$4/3*pi*L/2*H/2*W/2 (pi=3.14)$

When the height cannot be measured, the formula:

Tumor size=$4/3*pi*L/2*(W/2)^2$ was used for convenience. FIG. 6 shows the results.

As a result of the concomitant treatment with an existing antitumor agent and an Burdock Fruit extract, when carboplatin and oxaliplatin were used, it was recognized that the tumor size was reduced 2.3-2.1 times (P<0.05) compared to that of a single drug preparation of Burdock Fruit extract and 1.8-1.9 times (P<0.05) compared to that of a single drug preparation of each anticancer agent. In a case of irinotecan, it was recognized that the tumor size was reduced 2.1 times (P<0.05) compared to that of a single preparation of Burdock Fruit extract and 1.5 times compared to that of a single preparation of the anticancer agent.

In doxorubicin, it was recognized that the tumor size was reduced 1.4 times compared to that of a single preparation of Burdock Fruit extract and about 1.5 times (P<0.05) compared to that of a single preparation of the anticancer agent. In everolimus, it was recognized that the tumor size was reduced 2.1 times (P<0.05) compared to that of a single preparation of Burdock Fruit extract and 1.4 times compared to that of a single preparation of the anticancer agent. In bortezomib, it was recognized that the tumor size was reduced 1.8 times (P<0.05) compared to that of a single preparation of Burdock Fruit extract and 1.4 times compared to that of a single preparation of the anticancer agent. In a case of hydroxychloroquine which is a therapeutic agent for malaria or autoimmune disease, it was recognized that the tumor size was reduced 1.9 times compared to that of a single preparation of Burdock Fruit extract and 2.5 times (P<0.05) compared to that of a single preparation of the anticancer agent (see FIG. 6).

From the above described results, it has been shown that the Burdock Fruit extract rich in arctigenin is expected to be a drug having a potent antitumor effect in combination with an existing anticancer agent having a variety of drug effect mechanisms.

Test Example 7

The effect of a combined treatment with a Burdock Fruit extract rich in arctigenin and bevacizumab for colorectal cancer was examined. As bevacizumab, Avastin was used.

Bevacizumab suppresses the angiogenesis by inhibiting the action of vascular endothelial growth factor (VEGF), and suppresses the growth and metastasis of tumor. By administering bevacizumab, the angiogenesis in tumor is inhibited and a hypoxia and undernutritional environment is generated; furthermore by combining arctigenin, arctigenin considered to exhibit the antitumor effect against the tumor placed in the hypoxia and undernutritional environment.

It has been elucidated that arctigenin has a marked activity to the cancer stem cells existing in pancreatic tumor having the resistance to hypoxia and undernutrition at an individual level of mouse. As shown in Test Example 1, it has been shown that arctigenin can enhance decrease of the cancer stem cells by combining with gemcitabine.

It has been reported that colorectal cancer exhibits the resistance to hypoxia and undernutrition similarly to pancreas cancer, and since there were many patients, it was intended to evaluate the effect of combination of bevacizumab and a Burdock Fruit extract to the cancer stem cells in the colorectal tumor.

(Preparation of Transplanted Mouse and Therapeutic Test)

Human colorectal cancer cells LS174T (ATCC, CL-188) ($5 \times 10^5$ cells) were subcutaneously transplanted to BALB/cAJc1-nu/nu mice (CLEA Japan). On the 14th day, the transplanted mice were divided into 4 groups, that is, (a) an untreated group, (b) a bevacizumab-administered group, (c) a Gogoshi extract-administered group, and (d) a group of combined administration of a Burdock Fruit extract and bevacizumab (combined administration group), and the treatment was continued for 4 weeks. When a Burdock Fruit extract was administered, 250 mg/kg of Burdock Fruit extract (25 mg/kg as arctigenin) of Example 1 was orally administered 6 times a week. Bevacizumab, as Avastin for intravenous drip injection (100 mg/4 ml) (Chugai Pharm. Co.), was intraperitoneally injected at a dose of 5 mg/kg once a week.

(Tumor Weight)

After termination of the therapeutic test, the tumor weight was measured in the respective groups. As results, the tumor weight after termination of the therapeutic test was as follows: 2.51 g in the untreated group, 1.33 g in the bevacizumab administered group, 1.25 g in the Burdock Fruit extract administered group, and 0.68 g in the combined administration group. Accordingly, in any group including the bevacizumab administered group, the Burdock Fruit extract administered group and the combined administration group, the inhibition of increase of tumor weight was recognized compared with the untreated group. In addition, in the combined administration group, the stronger inhibition of increase of tumor weight was recognized than in the single administration.

(Proportion of Cancer Stem Cells in Tumor)

The cancer cells were then recovered from the tumor tissue, and using the double positive markers, CD133 and CD44, the proportion of CD133$^+$, CD44$^+$ cells in tumor after termination of the treatment test was evaluated by means of a FACS ARIA II flow cytometer (BD bioscience). The proportion was determined by treating the cells existing in tumor with TruStain fcX (mouse, biolegend), eliminating the dead cells with Sytox-Red (Invitrogen) and eliminating the cells of mouse origin with a mouse lineage cocktail (biolegend), anti-H2-Kd (biolegend) to give the proportion in the remaining pancreatic cancer cells ($2.5 \times 10^4$).

As a result, the proportion of CD133$^+$, CD44$^+$ cells (double positive) in tumor after termination of the treatment test was as follows: 0.16% in the untreated group, 0.552% in the bevacizumab administered group, 0.304% in the Burdock Fruit extract administered group, and 0.056% in the combined administration group. Accordingly, in the combined administration group, decrease of the proportion of the cancer stem cells in tumor was recognized compared with that of untreated group and the single administration group.

From these results, it has been shown that the combination of a Burdock Fruit extract and bevacizumab can suppress the growth of tumor and reduce the proportion of colorectal cancer stem cells in tumor which possibly causes the recurrence of tumor, distant metastasis and occurrence of resistance to anticancer agents. In addition, in Test Example 2 as described above, the survival benefit was shown by combination of Burdock Fruit and bevacizumab. Accordingly, it has been shown that a concomitant preparation of Burdock Fruit extract and bevacizumab exhibits a remarkably higher anticancer activity than that expected from the single administration of the respective ones.

Test Example 8

As for a Burdock Fruit extract and gemcitabine, a toxicity test by concomitant repeated-dose administration was conducted.

SIX SCR-ICR mice (female of 6 weeks of age) (SLC Co.) were used in each of 4 groups, that is, (a) untreated group, (b) gemcitabine administered group, (c) Burdock Fruit extract administered group, and (d) group of combined administration of Burdock Fruit extract and gemcitabine (combined administration group). In each group, each of the therapeutic agents was administered continuously for a period of 7 weeks.

Burdock Fruit extract, 250 mg/kg prepared in Example 1 (25 mg/kg as arctigenin), was orally administered 5 times a week. As gemcitabine, an intravenous drip preparation of gemcitabine (Eli Lilly and Co.) was used, and 100 mg/kg was intraperitoneally administered once a week.

During the term of administration for about 7 weeks, measurement of body weight, observation of skin and oral state, as well as observation of feces were practiced every 5 days. As a result, there was recognized no symptom which reminded any side effect such as inflammation in skin and mucous membrane, depilation or diarrhea in all of the administered groups. In addition, generally there was no difference of significance in body weight which is an indicator of nausea, loss of appetite, side effect in digestive system, and the like.

After termination of administration, the mice were anesthetized deeply, subjected to thoracotomy and complete blood drawing from heart. In addition, kidney, liver, spleen and lung were recovered, the weight was measured.

FIG. 7 shows the results of weight measurement of kidney, liver, spleen and lung as well as the rate (%) of their weight/body weight in the respective groups. As shown in FIG. 7, in the gemcitabine-administered group, it was recognized that the weight/body weight rate (%) of liver and spleen lowered about 20% compared with that of the untreated group. On the other hand, there was a tendency to recover the lowering in the combined administration group.

In addition, a hemocytic and biochemical examination was carried out using the collected blood. FIG. 8 shows the results.

The number of leukocytes was slightly lower in the gemcitabine administered group than the standard range of female SLC-ICR mice of 10 weeks of age, and in comparison with the untreated group, lowering to approximately 50% was recognized. On the other hand, in a case of the combined administration of a Burdock Fruit extract and gemcitabine, the lowering was controlled to approximately 75% compared with the untreated group; this value fell practically within the standard range.

Similarly, the number of erythrocytes was slightly lower in the gemcitabine administered group than the standard range, and in comparison with the untreated group, lowering to approximately 87% was recognized. On the other hand, in a case of the combined administration of a Burdock Fruit extract and gemcitabine, the value was recognized to return almost to that of the untreated group.

Similarly in a case of the numbers of leukocytes and erythrocytes, the lowering of hemoglobin and hematocrit values observed in the single administration of gemcitabine had a tendency to recover by the combined administration.

The number of platelets was recognized to rise approximately 110% in the Burdock Fruit extract-administered group compared to that of the untreated group. On the other hand, in the gemcitabine-administered group, lowering to approximately 70% was recognized in comparison with that of the untreated group. When a Burdock Fruit extract and gemcitabine were concomitantly administered, the value was recognized to recover up to approximately 92% of that of the untreated group.

Therefore, it has been elucidated that when a Burdock Fruit extract produced according to a procedure of Example 1 is administered in combination with gemcitabine, decrease of hemocytes can significantly be inhibited.

In addition, hepatopathy markers, AST and ALT, in the gemcitabine-administered group were recognized to rise 46% and 102% respectively compared to the untreated group; particularly, AST deviated from the standard range. On the other hand, in the combined administration group of a Burdock Fruit extract and gemcitabine, the rising was suppressed to approximately 18% and 38% respectively, indicating the values falling within the standard range practically.

Therefore there was recognized no additional appearance and reinforcement of side effect in the combined administration of Burdock Fruit extract and gemcitabine. Rather, it has been suggested that the combined administration gives an effect of alleviating an adverse drug reaction such as bone marrow suppression or hepatopathy.

The present application is based on the Japanese Patent Application No. 2014-080895 which has been filed as of Apr. 10, 2014, which is hereby incorporated by reference in its entirety.

INDUSTRIAL APPLICABILITY

The present invention can be utilized suitably to drugs for treating or improving cancers or to food for preventing cancer.

The invention claimed is:

1. A method for normalizing intra-tumor blood vessels in a subject in need thereof, the method comprising administering an effective dose of arctigenin to the subject, whereby intra tumor blood vessels are normalized.

2. A method for enhancing drug delivery of a component having an anticancer activity to a tumor tissue in a subject in need thereof, the method comprising administering an effective dose of arctigenin to the subject, whereby drug delivery to said tumor tissue is enhanced.

3. A method for alleviating a lowering of the weight/body weight rate (%) of liver and spleen or hepatopathy caused by a component having an anticancer activity other than arctigenin in a subject in need of thereof, comprising administering an effective dose of arctigenin to the subject, whereby said weight/body weight rate (%) of liver and/or spleen or hepatopathy is lowered.

4. The method of claim 1, wherein the arctigenin is a Burdock fruit extract.

5. The method of claim 2, wherein the arctigenin is a Burdock fruit extract.

6. The method of claim 3, wherein the arctigenin is a Burdock fruit extract.

* * * * *